(12) United States Patent
Jaber et al.

(10) Patent No.: US 9,675,446 B2
(45) Date of Patent: Jun. 13, 2017

(54) PROSTHETIC IMPLANT FOR MEDIALIZATION THYROPLASTY

(71) Applicants: University of Pittsburgh—Of the Commonwealth System of Higher Education, Pittsburgh, PA (US); Loyola University Chicago, Maywood, IL (US)

(72) Inventors: James J. Jaber, Lombard, IL (US); Steven Charous, Northbrook, IL (US); Peter Wipf, Pittsburgh, PA (US); Christopher Siviy, Webster, NY (US); April J. Chambers, Glenshaw, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 20 days.

(21) Appl. No.: 14/772,344

(22) PCT Filed: Mar. 4, 2014

(86) PCT No.: PCT/US2014/020413
§ 371 (c)(1),
(2) Date: Sep. 2, 2015

(87) PCT Pub. No.: WO2014/138121
PCT Pub. Date: Sep. 12, 2014

(65) Prior Publication Data
US 2016/0008127 A1    Jan. 14, 2016

Related U.S. Application Data

(60) Provisional application No. 61/772,433, filed on Mar. 4, 2013.

(51) Int. Cl.
*A61F 2/20* (2006.01)
*A61M 16/04* (2006.01)

(52) U.S. Cl.
CPC ........ *A61F 2/20* (2013.01); *A61F 2210/0057* (2013.01); *A61F 2220/0025* (2013.01); *A61M 16/04* (2013.01)

(58) Field of Classification Search
CPC ...................................................... A61F 2/20
See application file for complete search history.

(56) References Cited

U.S. PATENT DOCUMENTS

| 5,197,982 A | 3/1993 | Goldsmith, III et al. |
| 5,201,765 A | 4/1993 | Netterville et al. |

(Continued)

OTHER PUBLICATIONS

International Search Report and Written Opinion of the International Searching Authority, mailed Jun. 3, 2014, for corresponding International Application No. PCT/US2014/020413, 11 pages.

(Continued)

*Primary Examiner* — Thomas J Sweet
*Assistant Examiner* — Wade P Schutte
(74) *Attorney, Agent, or Firm* — Klarquist Sparkman, LLP

(57) ABSTRACT

Systems and methods for medializing a paralyzed vocal cord are disclosed. In some embodiments, an apparatus includes a lateral portion, a medial portion, and a strut coupled to the lateral and the medial portions. Either the medial portion or the lateral portion can be adjustable in two dimensions which are not parallel to the length of the strut, which can also be adjustable. In some embodiments, the medial portion and/or the lateral portion can each comprise two adjustable arms and a base member which has a curvilinear configuration.

7 Claims, 16 Drawing Sheets

(56) References Cited

U.S. PATENT DOCUMENTS

| | | | |
|---|---|---|---|
| 5,358,522 A | 10/1994 | Montgomery et al. | |
| 5,549,673 A | 8/1996 | Beale | |
| 5,593,439 A | 1/1997 | Cummings et al. | |
| 5,693,096 A | 12/1997 | Bettez | |
| 2010/0023125 A1* | 1/2010 | Debry .................. | A61F 2/20 |
| | | | 623/14.11 |

OTHER PUBLICATIONS http://www.bosmed.com/thyroplasty.html, "Montgomery® Thyroplasty Implant System," Boston Medical Products, 5 pgs, printed Oct. 2012.

Ahmad, et al., "A Study of Incidence and Etiopathology of Vocal Cord Paralysis," *Indian Journal of Otolaryngology and Head and Neck Surgery*, vol. 54, No. 4, pp. 294-296 (Oct.-Dec. 2002).

Charous, Steven J., "Novel Technique of Silastic Implant Carving for Thyroplasty Type I Surgery," *Otolaryngology—Head and Neck Surgery*, 133, 629-630 (Oct. 2005).

Devos, et al., "Throplasty for Unilateral Vocal Fold Paralysis Using an Adjustable Implant in Porous Titanium," *European Annals of Otorhinolaryngogloy, Head and Neck Diseases*, 127, 204-212 (Nov. 2010).

Hoffman, et al., "Preliminary Investigation of Adjustable Balloon Implant for Type I Throplasty," *The Laryngoscope*, 121:793-800 (Apr. 2011).

Rosen, Clark A., "Medialization Laryngoplasty and Arytenoid Adduction," Section 3, Chapter 41 of *Operative Otolaryngology: Head and Neck Surgery, Larynx*, pp. 329-332, 2008.

* cited by examiner

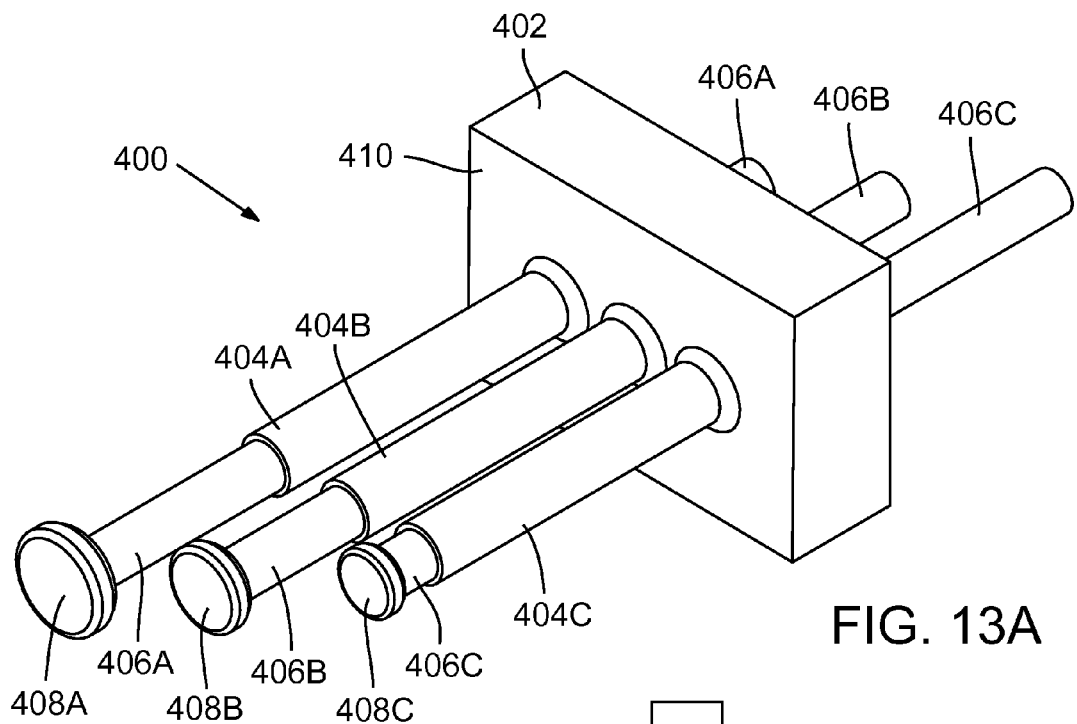
FIG. 13A
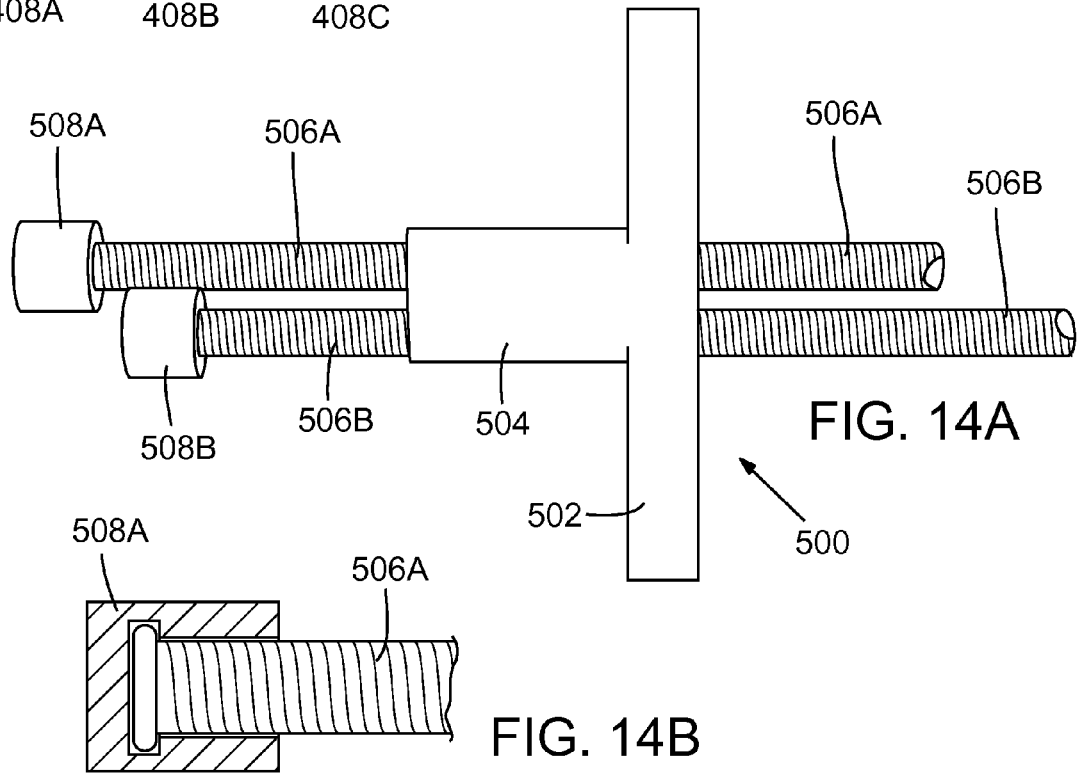
FIG. 14A
FIG. 14B

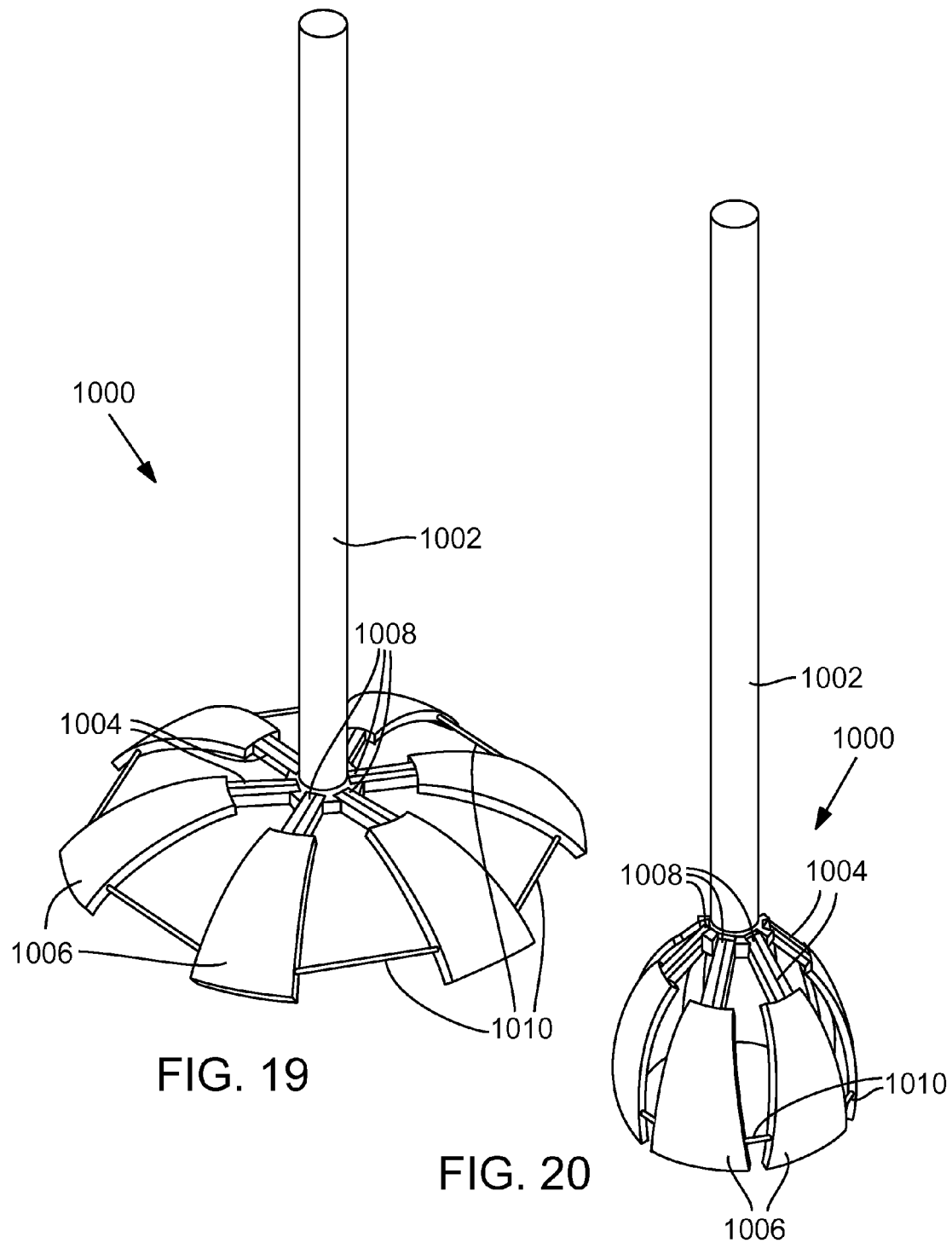

PROSTHETIC IMPLANT FOR MEDIALIZATION THYROPLASTY

CROSS REFERENCE TO RELATED APPLICATIONS

This application is the U.S. National Stage of International Application No. PCT/US2014/020413, filed Mar. 4, 2014, which in turn claims the benefit of and priority to U.S. Provisional Application No. 61/772,433, filed Mar. 4, 2013, which application is hereby incorporated herein by reference in its entirety.

FIELD

The present disclosure concerns embodiments of a thyroplant implant for performing medialization thyroplasty and related methods.

BACKGROUND

Human vocal folds, commonly known as vocal cords, help to regulate breathing, phonation and swallowing. The vocal cords are paired mucous membranes located in the larynx, which connects the pharynx and the trachea. Ordinarily, the vocal cords help produce speech by vibrating while a person exhales. The production of speech requires the vocal cords to be in close proximity to each other and vibrate as air is exhaled, thereby imparting oscillations (sound waves) into the passing air. The vocal cords help to regulate breathing by remaining open while a person breathes in or out and closed when a person is not breathing. They also remain closed during swallowing, helping to prevent food passing into the trachea.

Paralysis or impairment of a single vocal cord (unilateral vocal cord paralysis) can negatively affect a person's ability to breath, speak and swallow, and can be traced to neoplastic, iatrogenic, neurologic (Parkinson's, multiple sclerosis), congenital, or idiopathic causes, as well as to mechanical trauma. One specific cause is impairment of one of the recurrent laryngeal nerves, which help control the vocal cords. Vocal cord paralysis can occur at any age, though most commonly in older patients, and in both men and women. Paralysis of the left vocal cord is more common than paralysis of the right vocal cord, a fact attributable to the differences between the left and right recurrent laryngeal nerves. Another important cause of vocal cord impairment that is often overlooked is loss of vocal cord bulk, termed presbylaryngis, due to atrophy of the mucscular tone in the elderly population. Glottic cancer in which either surgical intervention through a cordectomy or with radiation treatment can also result in a decrease of vocal cord volume.

One known method of treating unilateral vocal cord paralysis is to medially displace the paralyzed vocal cord, thereby permitting it to approximate the functional vocal cord during phonation in a procedure sometimes referred to as medialization thyroplasty type II. One known method of doing so is cutting an opening in the thyroid lamina (which is made of cartilage), and mounting an implant on the cartilage in a way that pushes the non-functioning vocal cord medially, into the patient's glottis, and closer to the functional vocal cord. These methods can increase an individual's ability to speak and regulate breathing and prevent aspiration during swallowing by allowing the functional vocal cord to be substantially close the larynx.

Thyroplasty implants are known in the field. U.S. Pat. No. 5,358,522 to Montgomery, et al., describes an implant having a tiered base for anchoring in a window cut through the thyroid lamina and a projecting member for causing medial displacement of a vocal cord. Boston Medical Products Inc. markets thyroplasty implants made of soft silicone material under the Montgomery name, similar to those disclosed in the '522 patent. U.S. Pat. No. 5,549,673 to Beale describes an implant designed to be inserted through an opening in the thyroid cartilage, and which has a holding portion which facilitates insertion and allows the implant to be held in place by a shim. The literature also describes a triangular implant attached to a plate by a screw, and which is adjustable in one direction by turning the screw. Another known implant is an implantable balloon designed to be inflated with silicone to medialize the paralyzed vocal cord.

While these implants provide some benefits, they have several drawbacks. For example, in some cases they require proper sizing of the implants (such as by carving the implant itself) in order to be effective. Sizing of the implant is often determined during a procedure by implanting a test device and having the patient speak, thereby determining in real-time the benefits provided to the patient's phonation, but not assessment of aspiration. This method can increase the time required to complete a procedure and thus lead to increased trauma and edema in the patient's vocal cords, thereby reducing the effectiveness of the real-time testing (making it hard to discern to what degree improvements in phonation are due to the implant vs. due to edema). Further, balloon implants suffer from the drawback that their final shape is determined by the shape of the balloon itself: their shape is less customizable to individual patients. Finally, existing implants suffer complications such as persistent dysphonia, airway obstruction due to implant extrusion into the airway, and implant migration. In addition, commercially available implants may not be capable of closing large posterior gaps between the vocal cords, thereby necessitating an additional surgical procedure, an arytenoid adduction, to prevent aspiration. Accordingly, implants which can reduce trauma and edema that results from "trial and error" fitting of the various implants during the procedure, and implants with increased adjustability and tissue biocompatibility would be beneficial to prevent or reduce the aforementioned associated complications.

SUMMARY

Disclosed herein are embodiments of an invention allowing the medialization of a paralyzed vocal cord. In one embodiment, a prosthetic apparatus for displacing a vocal cord includes a lateral portion, an elongate strut, and a medial portion. The lateral portion is configured to be implanted against a thyroid lamina of a patient. The elongate strut has a first end portion coupled to the lateral portion, a second end portion, and a longitudinal axis defined by a line extending from the first end portion to the second end portion. The medial portion is coupled to the second end portion of the elongate strut and is configured to be implanted against a paralyzed vocal cord of the patient, and further configured to adjust a dimension of the medial portion in a plane that is not parallel to the longitudinal axis.

In other embodiments, a prosthetic apparatus is configured to adjust first and second dimensions of a medial portion, first and second dimensions of the lateral portion, and/or a dimension along the longitudinal axis. In other embodiments, the medial portion comprises a base member, a first adjustable arm, and a second adjustable arm. In other embodiments, the lateral portion comprises a base member, a first adjustable arm, and a second adjustable arm. In some embodiments, one of the base members comprises a curvilinear configuration. In some embodiments, one of the arms can comprise an inner portion and an outer portion which are slidably adjustable with respect to each other.

In another embodiment, a method of implanting a prosthetic apparatus comprises cutting an orifice into a thyroid lamina, inserting the prosthetic apparatus through the orifice, and positioning the prosthetic apparatus such that a lateral end portion is positioned adjacent to the thyroid lamina and a medial end portion is adjacent a vocal cord. The method in this embodiment further comprises adjusting a dimension of the prosthetic apparatus in a plane that is not parallel to a length of the apparatus extending from the lateral end portion to the medial end portion. In other embodiments, the method further comprises adjusting a dimension of the apparatus along the length of the apparatus extending from the lateral end portion to the medial end portion. In other embodiments, adjusting the apparatus includes adjusting the apparatus along a medial-lateral, anterior-posterior, and/or a superior-inferior anatomical axis.

In some embodiments, a prosthetic apparatus for displacing a vocal cord comprises a main body portion configured to be implanted against a thyroid lamina of a patient, the main body portion having a medial surface and a lateral surface and a plurality of lumen extending through the main body from the medial surface to the lateral surface of the main body, a plurality of engagement elements configured to engage a paralyzed vocal cord of a patient, and a plurality of pistons, each of the pistons having a first end portion situated within a respective one of the lumen of the main body and a second end portion coupled to a respective one of the engagement elements.

In some embodiments, a prosthetic apparatus for displacing a vocal cord comprises a main body portion configured to be implanted against a thyroid lamina of a patient, the main body portion having a medial surface and a lateral surface and a lumen extending through the main body from the medial surface to the lateral surface of the main body, an engagement element configured to engage a paralyzed vocal cord of a patient, a piston having a first end portion situated within the lumen of the main body and a second end portion coupled to the engagement element, and a retaining mechanism configured to be coupled to the main body and thereby prevent the piston passing out of the lumen through the lateral surface of the main body.

In some embodiments, a method of medializing a paralyzed vocal cord of a patient comprises inserting a prosthetic apparatus through an orifice in the patient's thyroid lamina, adjusting the location of at least one engagement element of the prosthetic apparatus by pushing a piston of the prosthetic apparatus coupled to the engagement element, whereby adjusting the location of the engagement element medializes at least a portion of the paralyzed vocal cord, and coupling a retaining mechanism to the prosthetic apparatus, thereby preventing the piston from moving laterally.

The foregoing and other objects, features, and advantages of the invention will become more apparent from the following detailed description, which proceeds with reference to the accompanying figures.

BRIEF DESCRIPTION OF THE DRAWINGS

FIGS. 13A-B illustrate another embodiment of a thyroplant implant.
FIGS. 14A-B illustrate another embodiment of a thyroplant implant.
FIGS. 19-20 illustrate an engagement portion of a thyroplant implant.

DETAILED DESCRIPTION

Figure 1A:
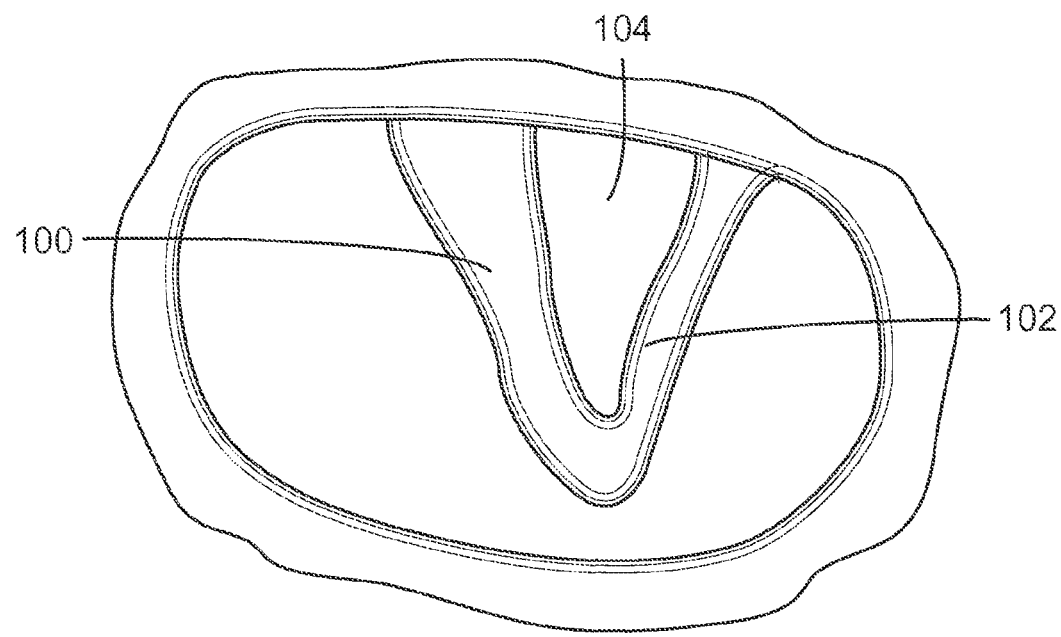
FIG. 1A illustrates vocal cords in an open configuration.
Figure 1B:
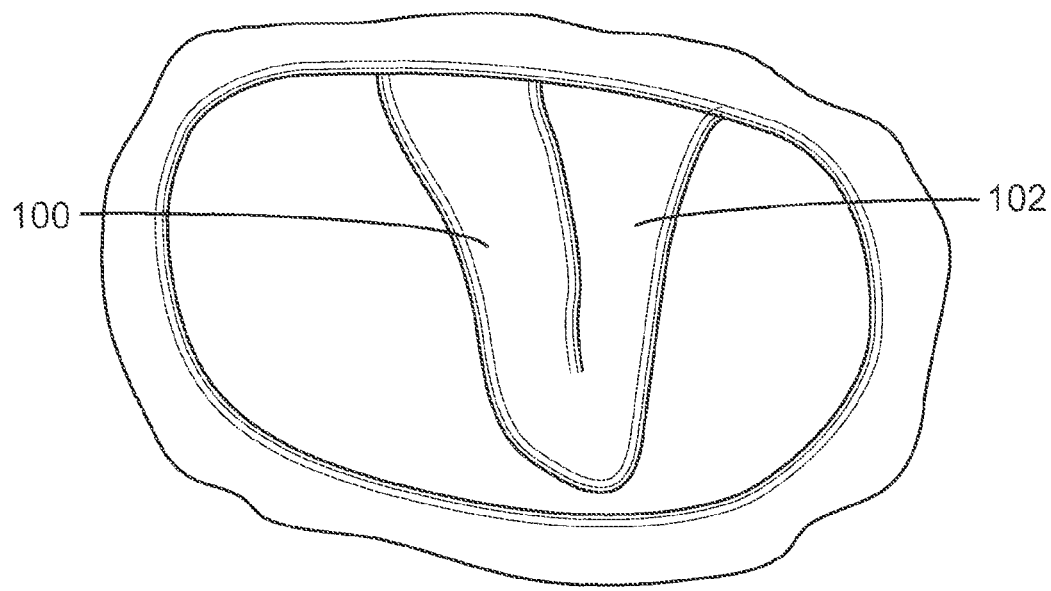
FIG. 1B illustrates vocal cords in a closed configuration.

FIGS. 1A-B illustrate a pair of vocal cords in both an open and a closed configuration, as viewed from the pharynx toward the trachea. As illustrated in FIG. 1A, a first vocal cord 100 and a second vocal cord 102 are in an open configuration, allowing air to pass between them, through the larynx 104 and the trachea, and into the lungs. As illustrated in FIG. 1B, the vocal cords 100, 102 are in a closed configuration, thereby reducing the volume of air passing between them. FIGS. 1A-B illustrate vocal cords which are fully functional: they are capable of opening and closing without medical intervention. If the first vocal cord 100 experiences paralysis, it is unable to move to the position illustrated in FIG. 1B and remains in the position illustrated in FIG. 1A. Similarly, if the second vocal cord 102 experiences paralysis, it is unable to move to the position illustrated in FIG. 1B and remains in the position illustrated in FIG. 1A. Thus, if one of the vocal cords 100, 102, experiences paralysis (a condition referred to as unilateral vocal cord paralysis), then even if the unaffected vocal cord shifts to the position illustrated in FIG. 1B, an opening remains through the larynx 104. Because the larynx helps to regulate breathing and speaking, and helps to prevent food passing to the trachea, unilateral vocal cord paralysis can cause a person to experience difficulty performing all of these functions.

Figure 2:
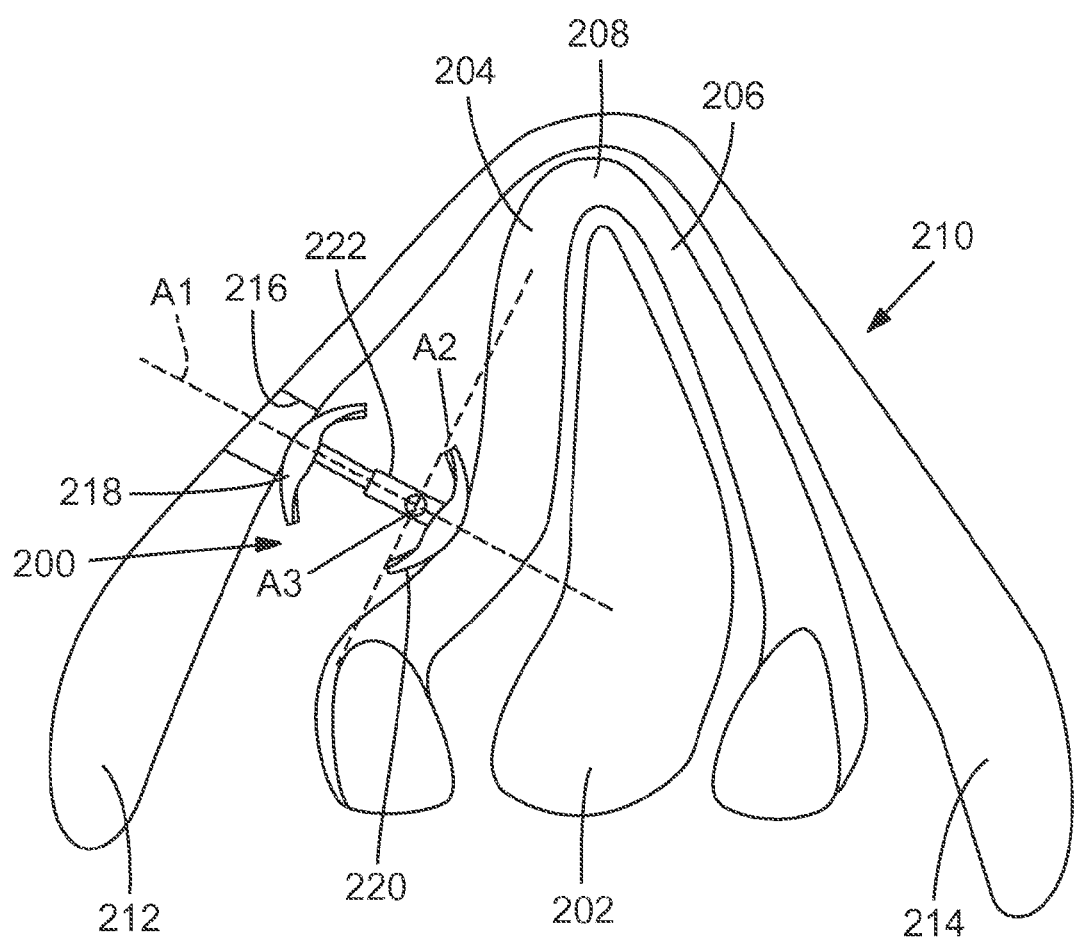
FIG. 2 illustrates one embodiment of a thyroplant implant positioned between a patient's thyroid lamina and vocal cord.
Figure 3A:
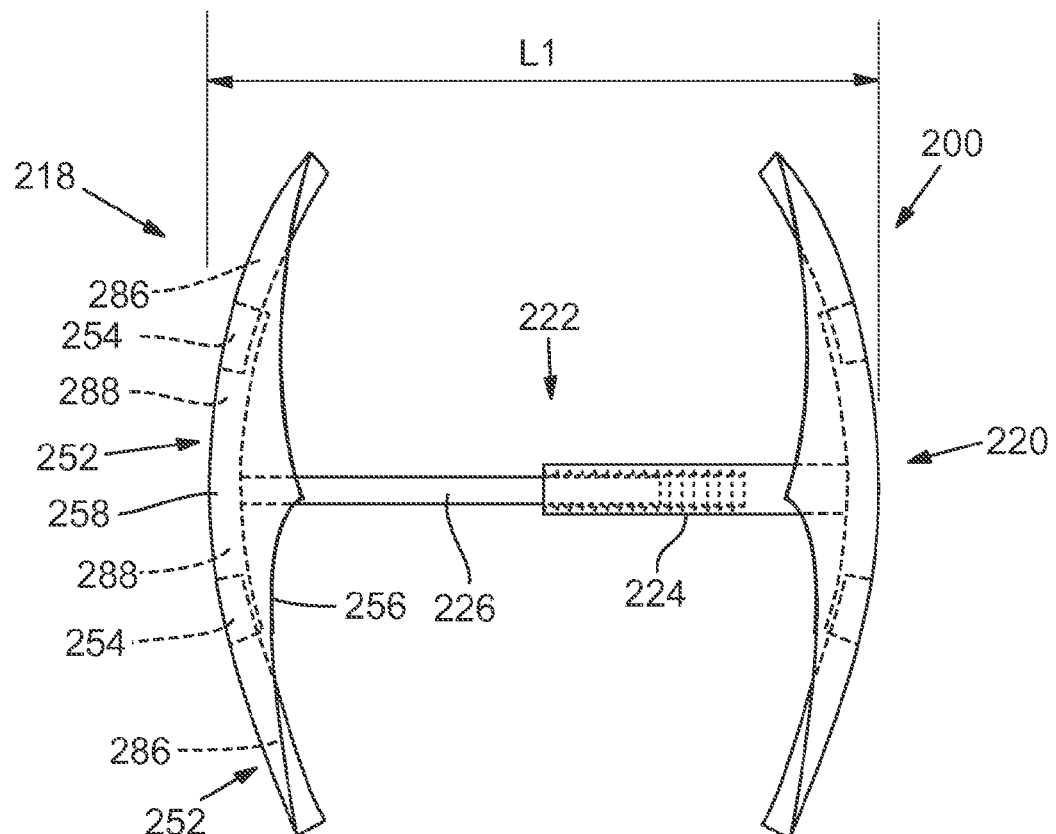
FIGS. 3A-B illustrate a side view of the implant of FIG. 2.
Figure 3B:
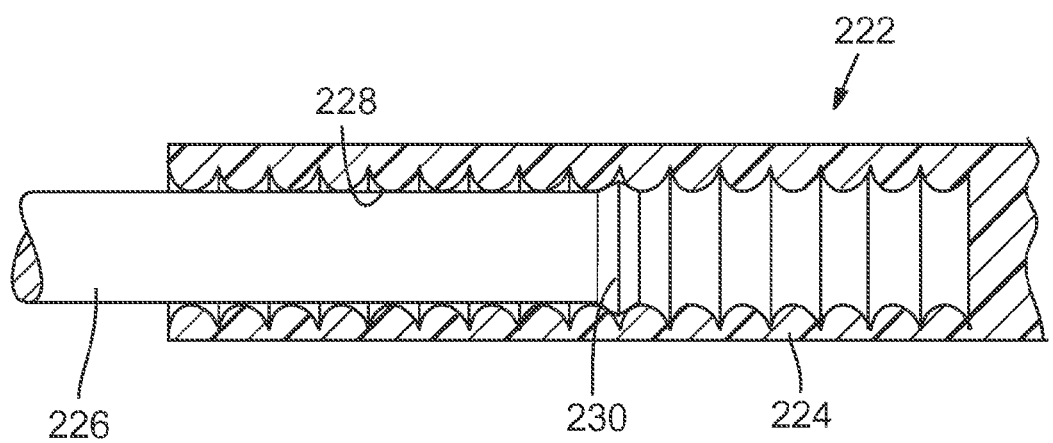
Figure 4:
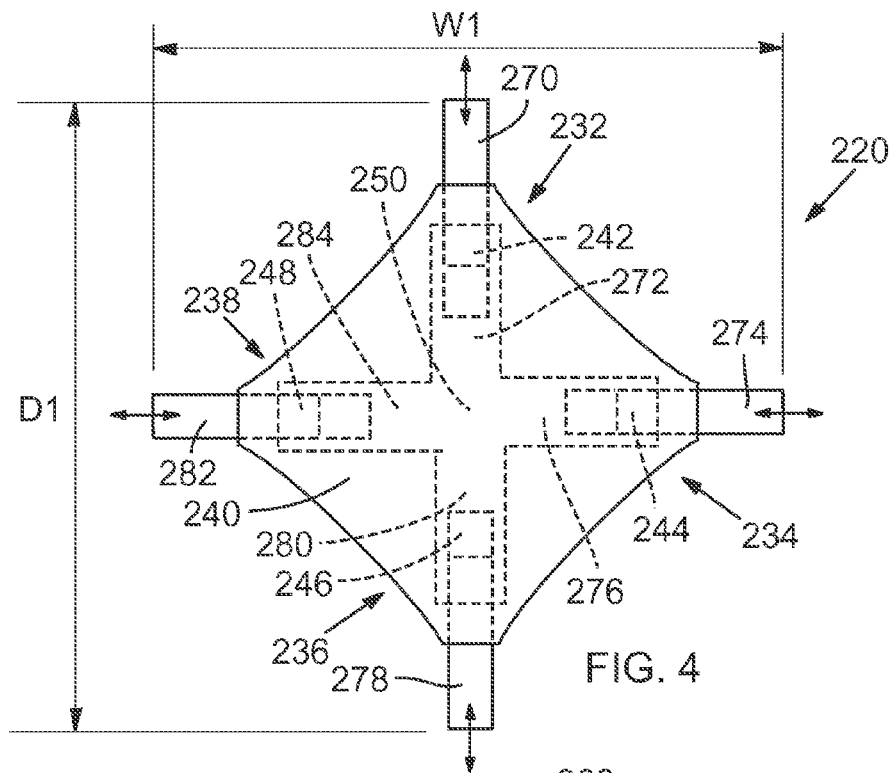
FIG. 4 illustrates an end view of the implant of FIG. 2.

FIGS. 2-4 illustrate a first embodiment of a thyroplant implant 200 which can be used to help treat a patient suffering from unilateral vocal cord paralysis or impairment, to improve the patient's ability to speak and breath, and to prevent aspiration. FIG. 2 illustrates the thyroplant implant 200 implanted in the region adjacent a patient's larynx 202. As illustrated, the larynx 202 is located between a paralyzed vocal cord 204 and a functional vocal cord 206 which meet at location 208. The paralyzed vocal cord 204 is located between the larynx 202 and a first portion 212 of the thyroid lamina 210, and the functional vocal cord 206 is located between the larynx 202 and a second portion 214 of the thyroid lamina 210. Other soft tissue and skin surround the thyroid lamina 210.

In order to insert the implant 200, a physician can incise the patient's soft tissue and dissect down to the thyroid cartilage and create an orifice 216 through the first portion 212 of the thyroid lamina 210. The physician can then introduce the implant 200 through the orifice 216. The thyroid lamina 210 is made of cartilage and thus provides a substantially rigid structure against which the implant 200 can be situated. As illustrated, the implant 200 is introduced such that a lateral end portion 218 is situated against the medial surface of the first portion 212 of the thyroid lamina 210 and a medial end portion 220 is situated against the lateral surface of the paralyzed vocal cord 204. In this configuration, the thyroid lamina 210 can, due to its rigidity, exert a force against the lateral end portion 218 of the implant 200, which is transferred through the implant 200 to the paralyzed vocal cord 204. Thus, by increasing the length of the implant 200 in the medial-lateral dimension, a physician can control the location of the paralyzed vocal cord 204. In this way, a physician can medially displace the paralyzed vocal cord 204 toward the functional vocal cord 206 such that the opening through the larynx 202 can be substantially closed by ordinary operation of the functional vocal cord 206.

As illustrated in FIGS. 2 and 3A, the lateral end portion 218 and the medial end portion 220 in the illustrated embodiment are each generally umbrella shaped. Another way of describing the shape of the end portions 218, 220 is that the end portions have a curvature similar to the surface of a sphere. This configuration provides some advantages but in alternative embodiments, various other configurations of the lateral end portion 218 and the medial end portion 220 can be used.

While any of a variety of techniques or mechanisms can be used to make the implant 200 adjustable, FIGS. 3A-B illustrate one specific implementation of an adjusting mechanism. As illustrated, the implant 200 includes a central strut 222 which includes two telescopically adjustable elements: an outer strut 224 and an inner strut 226. By inserting the inner strut 226 farther into the outer strut 224, the overall length L1 of the implant 200 is reduced, and by extracting the inner strut 226 from the outer strut 224, the overall length L1 of the implant 200 is increased.

As illustrated in FIG. 3B, a locking mechanism by which the length of the central strut 222 can be fixed after manual adjustment can include a set of teeth 228 on the inner surface of the outer strut 224 and a projection 230 extending radially outward from the outer surface of the inner strut 226. The shapes of the teeth and the projection can be configured such that a physician can manually apply force sufficient to cause the projection 230 to pass over the teeth 228, but ordinary forces experienced by the implant 200 in a patient's body will not cause the projection 230 to pass over the teeth 228 in either direction. In an alternative embodiment, the teeth 228 and/or the projection 230 could be spring loaded. In still other embodiments, other mechanisms could be used to fix the length L1 of the implant 200. For example, a pin or screw could be inserted radially through openings in the struts 224, 226 to prevent the struts from moving relative to each other. The pin could be spring loaded such that the pin is biased toward a position in which it extends through openings in the struts 224, 226 but can be manually shifted laterally out of one or both openings to permit adjustment of the struts 224, 226. In another embodiment, the struts 224, 226 can include complementary threaded end portions such that the length L1 can be adjusted by threading the inner strut 226 into or out of the outer strut 224. Finally, any other suitable mechanisms could be used.

As illustrated in FIG. 4, the medial end portion 220 of the implant 200 can include a first arm 232, a second arm 234, a third arm 236, and a fourth arm 238, each of which can be adjustable, and a first base member 240 generally shaped to resemble the canopy of an umbrella. The arms 232, 234, 236, and 238 can be mounted to the inside surface of the first base member 240 and can comprise structures similar to that of the central strut 222 for adjusting the lengths of the arms. Thus first arm 232 can include a first adjustment mechanism 242 connecting a first inner portion 270 and a first outer portion 272, second arm 234 can include a second adjustment mechanism 244 connecting a second inner portion 274 and a second outer portion 276, third arm 236 can include a third adjustment mechanism 246 connecting a third inner portion 278 and a third outer portion 280, and fourth arm 238 can include a fourth adjustment mechanism 248 connecting a fourth inner portion 282 and a fourth outer portion 284.

The overall width W1 of the medial end portion 220 is defined as the distance between the end of the second inner portion 274 and the fourth inner portion 282. The overall depth D1 of the medial end portion 220 is defined as the distance between the ends of inner portions 270, 278. The adjustability of the arms 232, 234, 236, and 238, and of the central strut 222, allows a physician to adjust the width W1, the depth D1, and the length L1 of the implant 200, and thereby facilitates more precise control over the final position of the paralyzed vocal cord 204. Thus, the implant 200 in this embodiment has at least three dimensions that are adjustable. The width W1 and depth D1 are measured in a plane that is perpendicular to the length L1 and a central axis of the strut 222.

The length L1 can be aligned with an axis A1 extending from the first portion of the thyroid lamina 212 to the paralyzed vocal cord 204. In use, the length L1 can be adjusted to adjust the distance between the thyroid lamina 210 and the paralyzed vocal cord 204 at the location of the implant 200. The width W1 can be aligned with an axis A2 extending from an anterior portion of the paralyzed vocal cord 204 to a posterior portion of the paralyzed vocal cord 204, and the depth D1 can be aligned with a superior-inferior anatomical axis A3. In use, the width W1 and the depth D1 can be adjusted to adjust the extent of contact between the end portion 220 and the paralyzed vocal cord 204. In particular embodiments, the width W1 can be adjusted to between 6 mm and 14 mm, the depth D1 can be adjusted to between 6 mm and 14 mm and the length L1 can be adjusted to between 5 mm and 15 mm.

As illustrated in FIG. 4, the outer arms 272, 276, 280, 284 can be formed integrally and thereby form a cross shaped central portion receiving each of the inner arms 270, 274, 278, 282. As illustrated in FIGS. 2-4, the central strut 222 and arms 232, 234, 236, and 238 can all meet at first connection location 250, located at the center of the cross shaped central portion. As illustrated, the central strut 222 can be oriented at a 90° angle from each of the arms 232, 234, 236, and 238, and each of the arms can be oriented at a 90° angle from two of the other arms. In alternative embodiments, these angles need not be 90° and can be any suitable angles. Similarly, in alternative embodiments, fewer or more than four arms can be used at either the medial end or the lateral end of a thyroplant implant. Also, as shown in FIG. 3A, the arms 232, 234, 236, 238 can be curved to match the curvature of the base member 240, like the ribs of an umbrella.

As illustrated in FIG. 3A, the lateral end portion 218 can have a structure similar to that of the medial end portion 220. Accordingly, the lateral end portion 218 can include four arms 252 (only two are pictured), each having an adjustment mechanism 254 that connects respective inner portions 286 and outer portions 288, and a second base member 256. The four outer portions 288 can be integrally formed and thereby form a cross shaped central portion receiving each of the four inner portions 286. The four arms 252 and the central strut 222 can be connected at a second connection location 258, and can be oriented at 90° angles from one another. Thus, the implant in the illustrated embodiment has at least five dimensions that are adjustable (the width and depth of the medial end portion 220, the width and depth of the lateral end portion 218, and the overall length).

Figure 5:
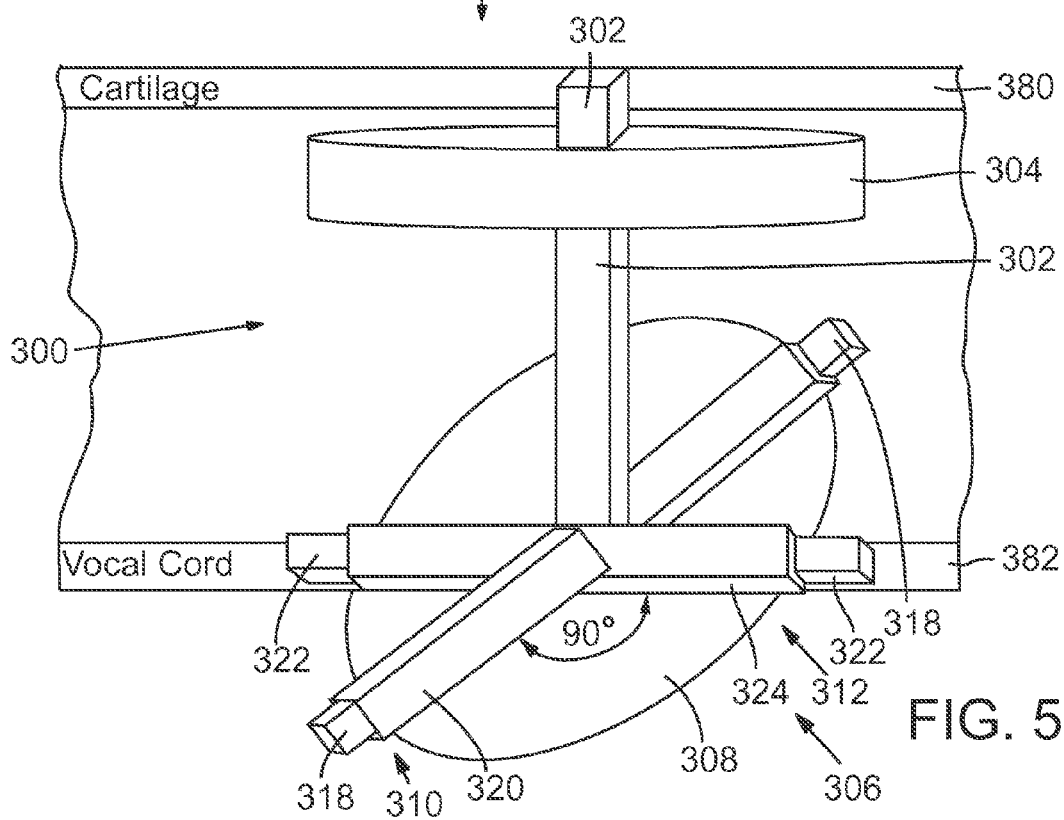
FIG. 5 illustrates another embodiment of a thyroplant implant.

FIGS. 5-12 illustrate a second embodiment of a thyroplant implant 300 which can be used to help treat a patient suffering from unilateral vocal cord paralysis and improve the patient's ability to speak, breath, and swallow properly. As illustrated in FIG. 5, the implant 300 includes a central strut 302, a lateral end portion 304, and a medial end portion 306. The lateral end portion 304 in the illustrated configuration comprises a flat, generally oval shaped member, and is designed to be situated against the medial surface of a patient's thyroid lamina 380. The lateral end portion 304 is further configured to be slidably adjustable along the length of the central strut 302, such that strut 302 can extend beyond the lateral surface of the lateral end portion 304. Once the lateral end portion 304 is adjusted to its desired location with respect to the central strut 302, the portion of the central strut 302 extending beyond the lateral end portion 304 can be removed, such as by cutting or severing that portion of the central strut 302.

The medial end portion 306 in the illustrated configuration includes a flat, generally circular shaped base member 308 and a first arm 310 intersecting a second arm 312 in a cruciform arrangement. The first arm 310 comprises two first inner portions 318 and a first outer portion 320, and the second arm 312 comprises two second inner portions 322 and a second outer portion 324. The first inner portions 318 are inserted into opposing ends of the outer portion 320 and can be extended out of or retracted into the outer portion 320 in a telescoping manner. Likewise, the second inner portions 322 are inserted into opposite ends of the outer portion 324 and can be extended out of or retracted into the outer portion 324 in a telescoping manner. Each of the arms 310, 312 includes an adjustment and locking mechanism connecting its respective inner and outer portions, as previously described. Any suitable adjustment mechanism can be used, including one similar to that described above for connecting the outer strut 224 and the inner strut 226 of the central strut 222. The medial end portion 306 is designed to be situated against the lateral surface of a patient's vocal cord 382.

Figure 6:
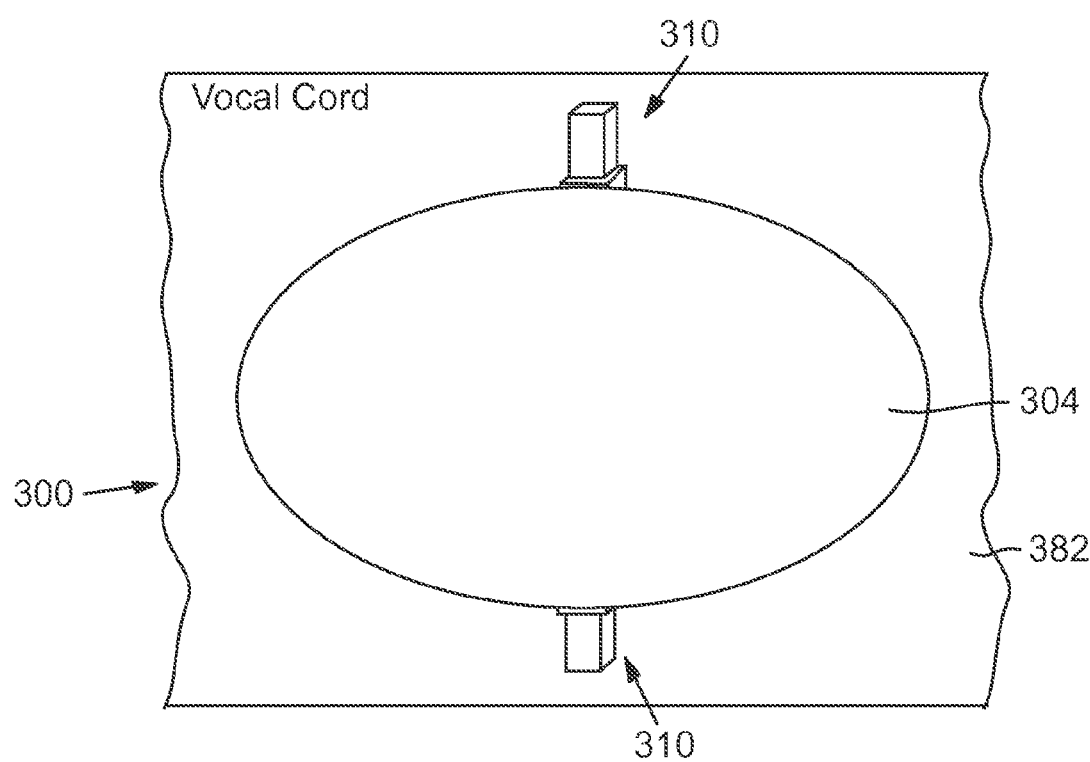
FIG. 6 illustrates a lateral end view of the implant of FIG. 5.
Figure 7:
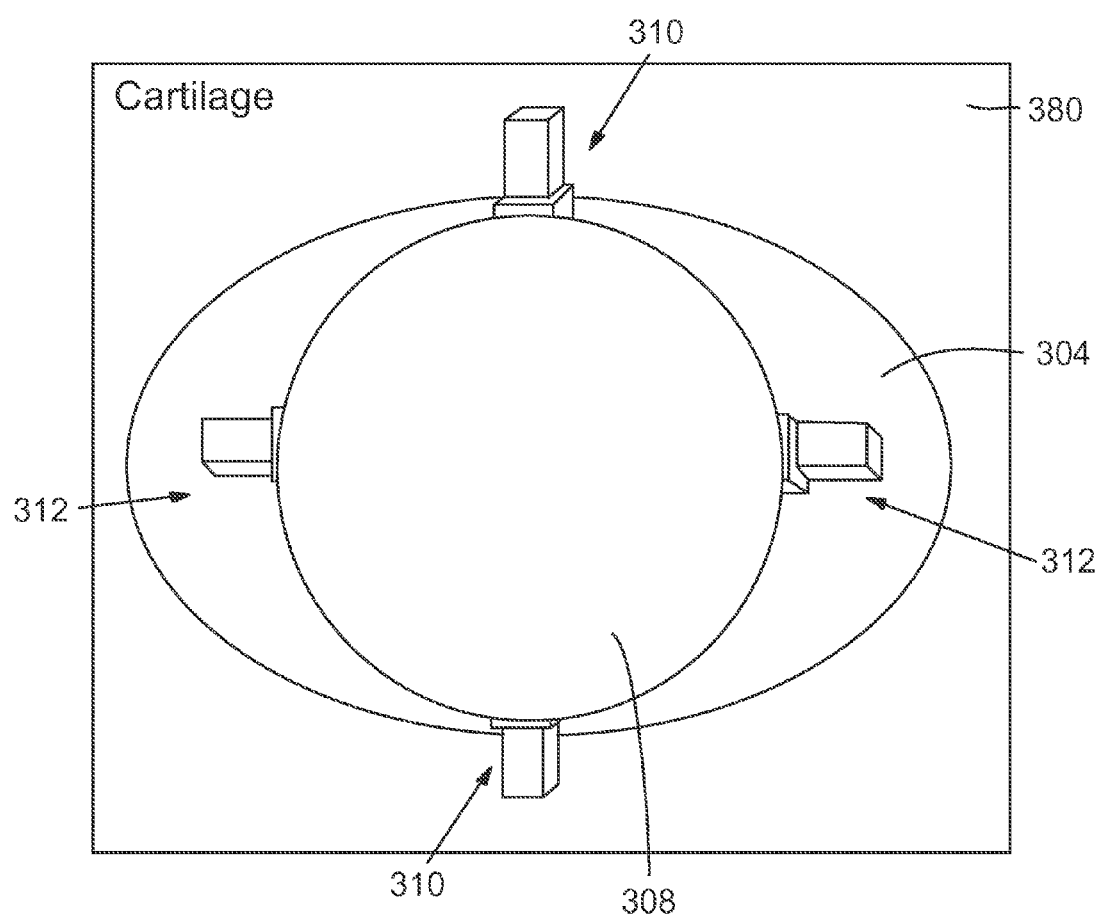
FIG. 7 illustrates a medial end view of the implant of FIG. 5.

FIG. 6 illustrates the implant 300 from a lateral end view, along the axis of the central strut 302, with the patient's vocal cord 382 in the background. Visible elements of the implant 300 include the lateral end portion 304 and the first arm 310. FIG. 7 illustrates the implant 300 from a medial end view, along the axis of the central strut 302, with the patient's thyroid lamina 380 in the background. Visible elements include the lateral end portion 304, the circular member 308 of the medial end portion 306, and both arms 310 and 312. As illustrated most clearly in FIG. 7, the lateral end portion 304 can be generally oval shaped and can be larger than the circular base member 308 of the medial end portion 306. In alternative embodiments, various shapes and sizes can be used for each of the lateral end portion 304 and the base member 308. Further, although they are flat in the illustrated embodiments, members 304, 308 can be curved similar to the end portions of the implant 200.

Figure 8A:
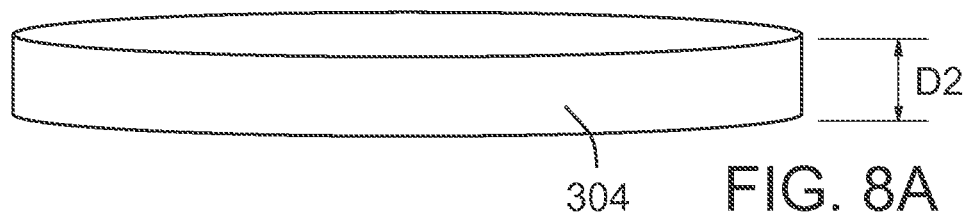
FIGS. 8A-B illustrate a lateral end portion of the implant of FIG. 5.
Figure 8B:
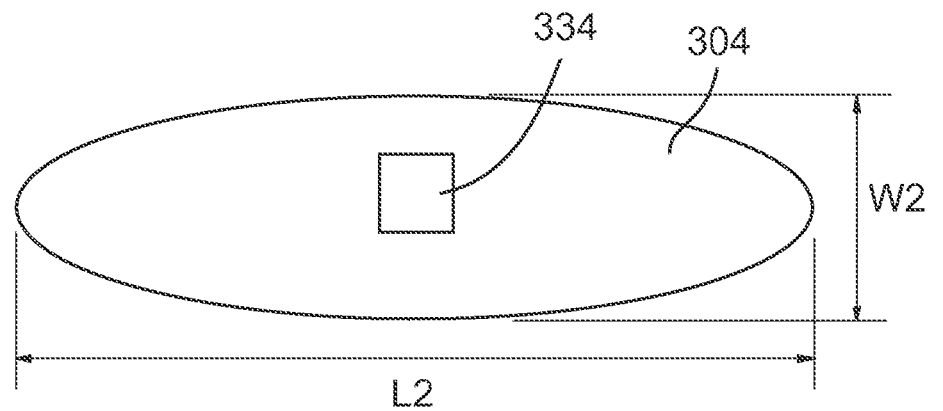
Figure 9A:
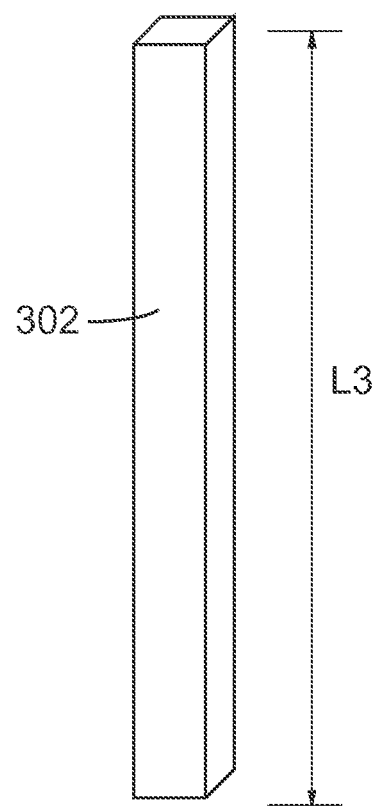
FIGS. 9A-B illustrate a strut portion of the implant of FIG. 5.
Figure 9B:
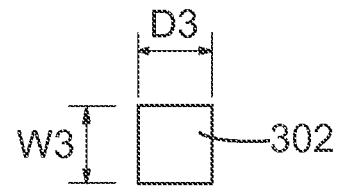
Figure 10A:
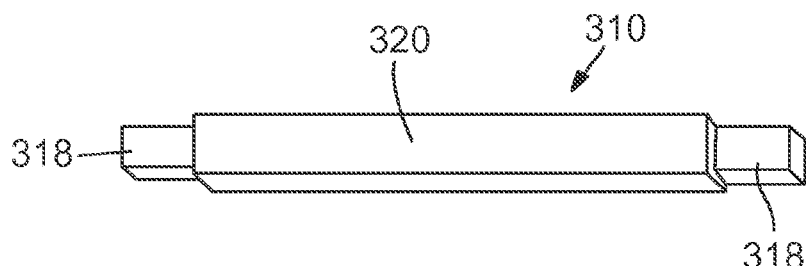
FIGS. 10A-E illustrate a first arm portion of the implant of FIG. 5.
Figure 10B:
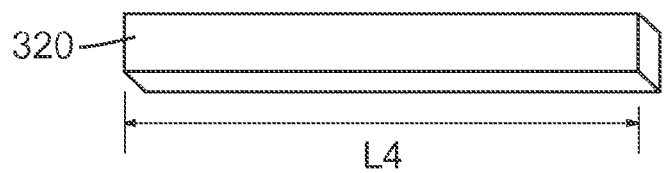
Figure 10C:
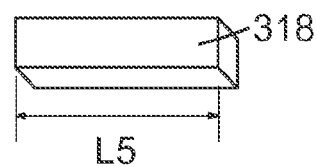
Figure 10D:
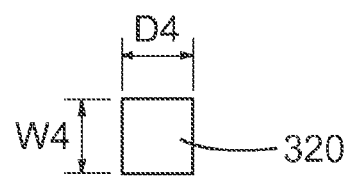
Figure 10E:
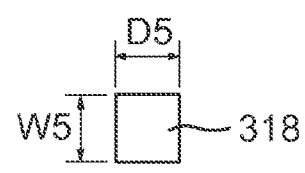

FIGS. 8A and 8B illustrate the lateral end portion 304 in isolation, from a side view and a top view, respectively. As illustrated, the lateral end portion 304 has a length L2 of about 10 mm, a width W2 of about 6 mm, and a depth D2 of about 2 mm. It also has an opening 334 at its center having dimensions of about 2 mm by about 2 mm to accommodate insertion of the central strut 302. FIGS. 9A and 9B illustrate the central strut 302 in isolation, from a side view and an end view, respectively. As illustrated, the central strut has a length L3 of about 15 mm, a width W3 of about 2 mm, and depth D3 of about 2 mm FIGS. 10A-10E illustrate components of the first arm 310 in isolation. As shown in FIG. 10A, each of the inner portions 318 is positioned within and telescopically adjustable with respect to the outer portion 320. As illustrated in FIGS. 10B and 10D, the outer portion 320 has a length L4 of about 6 mm, a width W4 of about 2 mm, and a depth D4 of about 2 mm, and as illustrated in FIGS. 10C and 10E, the inner portions 318 have a length L5 of about 4 mm, a width W5 of about 1.95 mm, and a depth D5 of about 1.95 mm.

Figure 11A:
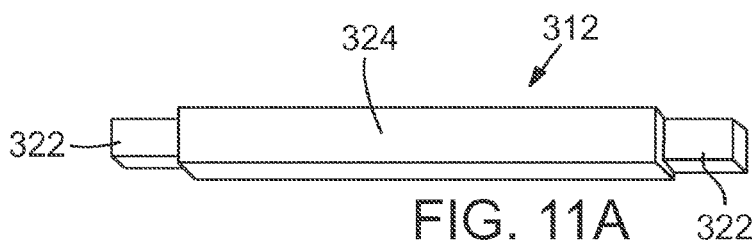
FIGS. 11A-E illustrate a second arm portion of the implant of FIG. 5.
Figure 11B:
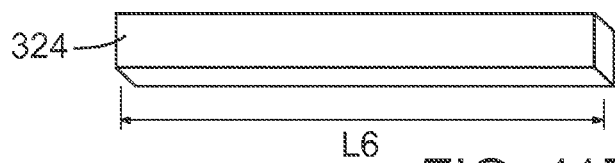
Figure 11C:
Figure 11D:
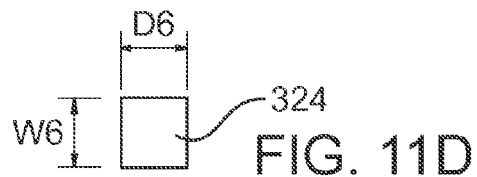
Figure 11E:
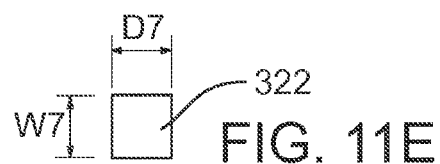
Figure 12A:
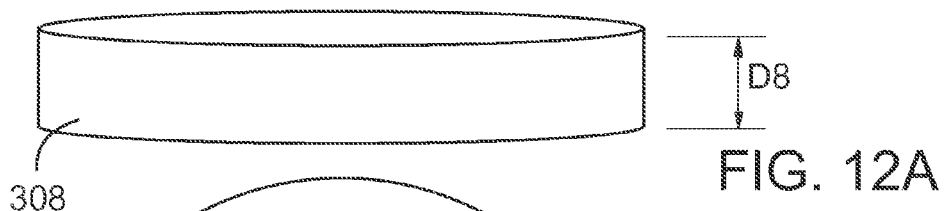
FIGS. 12A-B illustrate a circular portion of the medial end portion of the implant of FIG. 5.
Figure 12B:
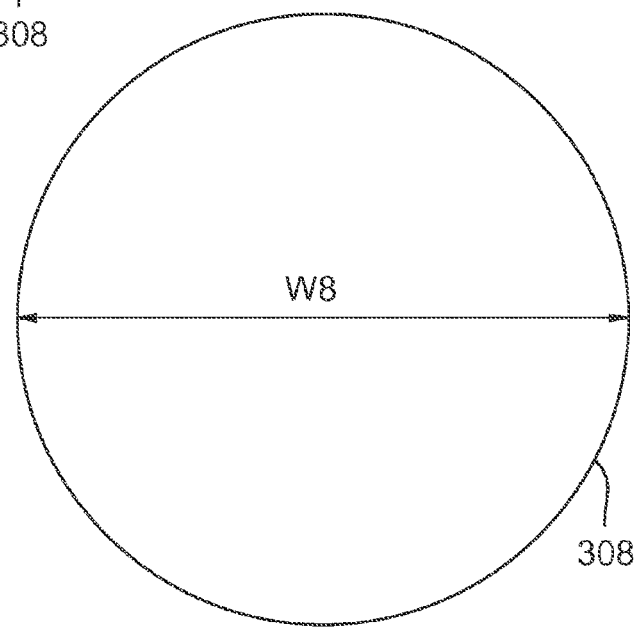

FIGS. 11A-11E illustrate components of the second arm 312 in isolation. As shown in FIG. 11A, each of the inner portions 322 is positioned within and telescopically adjustable with respect to the outer portion 324. As illustrated in FIGS. 11B and 11D, the outer portion 324 has a length L6 of about 8 mm, a width W6 of about 2 mm, and a depth D6 of about 2 mm, and as illustrated in FIGS. 11C and 11E, the inner portions 322 have a length L7 of about 4 mm, a width W7 of about 1.95 mm, and a depth D7 of about 1.95 mm FIGS. 12A-12B illustrate the circular shaped member 308 of the medial end portion 306 in isolation, from a side view and an end view, respectively. As illustrated, the circular shaped member 308 has a width or diameter W8 of about 6 mm, and a depth or thickness D8 of about 2 mm. It should be noted that the dimensions provided above and shown in FIGS. 8-12 represent one specific implementation of the implant 300. Any of these dimensions can vary based on the particular application.

Figure 13B:
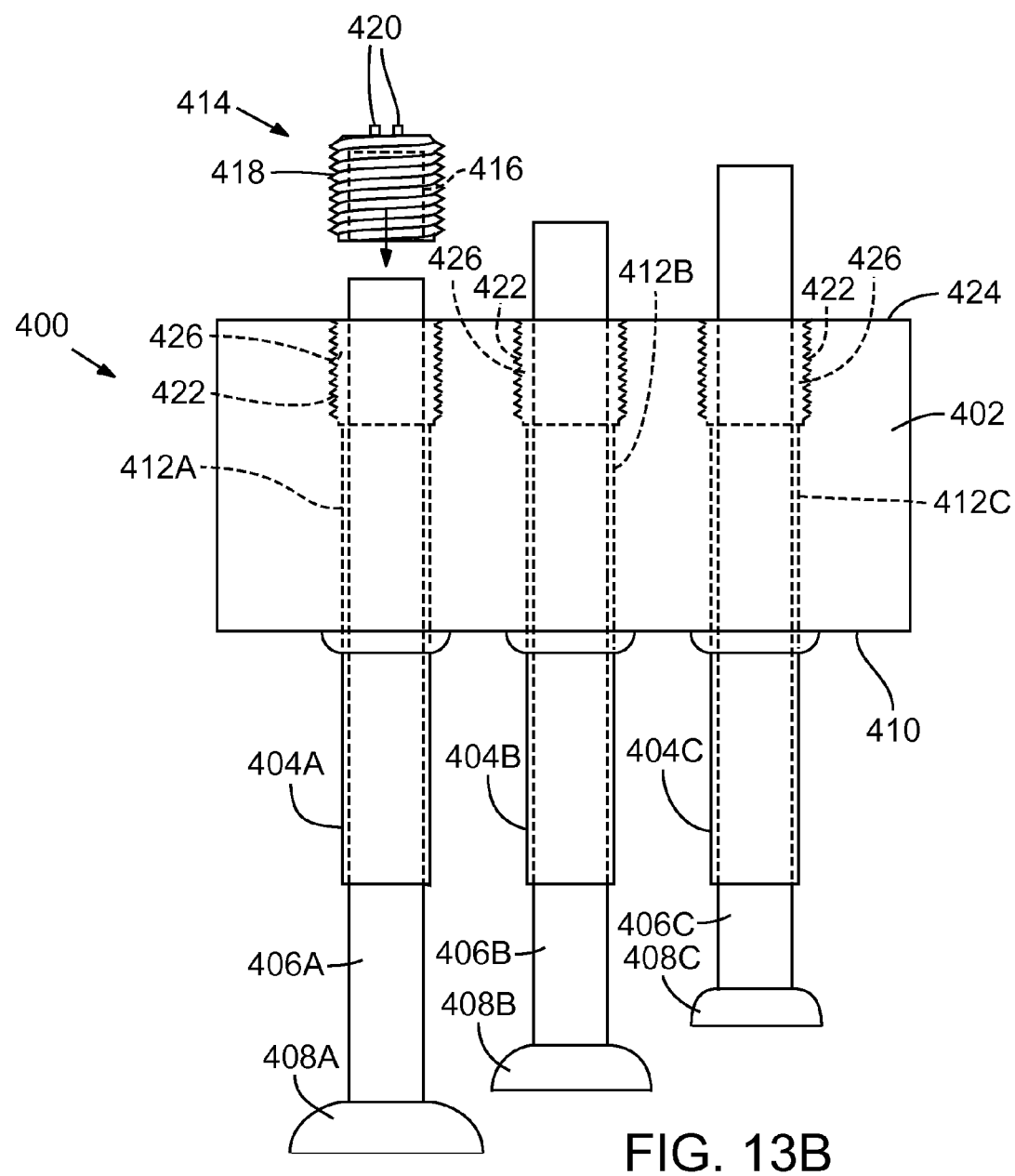

FIGS. 13A-13B illustrate another embodiment of a thyroplant implant 400. As illustrated in FIGS. 13A and 13B, implant 400 can include a main body 402 having a shape comprising, for example, a rectangular prism. Implant 400 can also include three sleeves 404A, 404B, 404C extending outward from a medial surface 410 of the main body 402. The sleeves 404A-404C can be hollow, and can include internal lumen coupled to respective lumen 412A, 412B, 412C, extending through the main body 402. The implant 400 can also include three pistons 406A, 406B, 406C, extending through and axially adjustable with respect to the sleeves 404A-404C and respective lumen 412A-412C extending through the main body 402. While the pistons 406A-406C and sleeves 404A-404C are shown as circular in the illustrated embodiment, and thus can rotate with respect to one another, in other embodiments, the pistons and sleeves can have non-circular shapes, e.g., to prevent their rotation with respect to one another. The sleeves 404 can act to stabilize the pistons 406 and to help maintain their position and orientation with respect to the main body 402. As illustrated, the three pistons 406A-406C can be spaced apart from one another along an axis aligned with the longest dimension of the main body 402, which can be substantially longer than the other two dimensions of the main body 402. In alternative embodiments, however, alternative arrangements of the pistons and shapes of the main body 402 can be used.

The implant 400 can also include three medial engagement portions 408A, 408B, 408C, each coupled to a medial end portion of a respective one of the three pistons 406A-406C. As shown in FIGS. 13A-13B, a first engagement portion 408A can be larger than (e.g., have a larger diameter than) a second engagement portion 408B, which can be larger in turn than a third engagement portion 408C. In the illustrated embodiment, each of the engagement portions 408A-408C have round cross-sectional profiles (in a plane perpendicular to the lengths of the pistons), but in alternative embodiments, the engagement portions can comprise any of a variety of suitable shapes in cross-section, such as ovals, squares, triangles, stars, cruciform shapes, etc.

As shown in FIG. 13B, the implant 400 can also include a locking cap 414 which can include a round hollow main body having a cavity 416, a series of threads 418 formed in an exterior surface of the cap 414, and tool engagement elements 420 on a lateral end portion of the cap 414. The main body 402 can include three recesses 426 formed in a lateral surface 424 of the main body 402 and coupled to respective lumen 412A-412C. Each of the recesses 426 can include an annular surface having threads 422 formed therein, the threads 422 being complementary to the threads 418 of the cap 414.

In order to insert the implant 400, a physician can cut through a patient's skin and soft tissue and create an orifice through the patient's thyroid lamina, as described above. The orifice can have an elongated shape which is substantially longer along the axis A2 (FIG. 2) than along the axis A3 (FIG. 2), such that the orifice is substantially aligned with the paralyzed vocal cord. The physician can then introduce the implant 400 through the orifice with the longest dimension of the main body 402 aligned with and parallel to the axis A2, such that the pistons are aligned with the paralyzed vocal cord, and such that the largest engagement portion 408A is located nearest the posterior end of the paralyzed vocal cord and the smallest engagement portion 408C is located nearest the anterior end of the paralyzed vocal cord. In some cases, the main body 402 can be physically coupled to the thyroid lamina, such as by any mechanical fastener, and as one example, the main body can be screwed to the thyroid lamina once in place in order to prevent it moving from a desired location.

This arrangement can be advantageous because the posterior ends of the vocal cords typically have a larger surface area than the anterior ends of the vocal cords, and because the posterior ends of the vocal cords, which are closer to the esophageal inlet, are typically spaced farther from one another than the anterior ends of the vocal cords, and thus must be displaced farther to treat vocal cord paralysis and to close the posterior gap to prevent aspiration. Due to both of these factors, it can be advantageous to exert a greater force against the posterior end of a paralyzed vocal cord. Thus, providing a larger engagement portion at the posterior end of the paralyzed vocal cord can help to reduce the total pressure exerted against it, thereby reducing trauma to the native tissues. This can reduce or eliminate the need for the aforementioned arytenoid adduction procedure, thereby minimizing the number of surgical procedures a patient must undergo to treat vocal cord impairment and dysphagia.

Once the implant 400 has been introduced through the orifice, the physician can adjust the locations of the engagement portions 408 by pushing the pistons 406 through the main body 402 (e.g., manually or by other mechanisms). Thus, the physician can manipulate the location of the paralyzed vocal cord and monitor the resulting changes in the patient's phonation. Providing pistons 406 which can be pushed directly through the main body 402, e.g., rather than threading through the main body 402, can reduce resulting trauma to the native tissues. Once the physician observes improved or optimal changes in phonation through the adjustments of the pistons, the locations of the pistons 406 with respect to the main body can be noted, and excess lengths of the pistons 406 (i.e., the length of the pistons extending from the lateral surface 424 of the main body) can be removed. The physician can then screw the three caps 414 into the recesses 426 in the main body 402, thereby locking the pistons 406 (and thus the engagement portions 408) in place (in the locations with respect to the main body 402 noted as corresponding to improved or optimal changes in phonation) and preventing them from being pushed laterally through the main body 402. For example, the physician can use a screwdriver to engage the engagement elements 420 of the cap 414 and screw the cap 414 into the main body 402, as the main body 402 can have been previously affixed to the thyroid cartilage by any mechanism described herein (e.g., using slots such as slots 1108A, 1108B), thus providing resistance to the applied force of screwing the cap in place. In some cases, alternative engagement elements can used (e.g., engagement elements can be recessed into the surface of the cap 414 rather than protruding therefrom) and the main body and caps 414 can together have a flush or substantially flush lateral surface. The physician can then close the orifice and any other of the patient's tissues as needed.

FIGS. 14A and 14B illustrate another embodiment of a thyroplant implant 500. Implant 500 includes a main body 502, a sleeve 504, two threaded rods 506A, 506B, and two engagement portions 508A, 508B. The threaded rods 506A, 506B can be, for example, commercially available M2 threaded rods. The main body 502 and the sleeve 504 include internal threaded lumen through which the threaded rods 506 are threaded. Implant 500 can include caps (not illustrated) and other features similar to those described above with respect to implant 400. FIG. 14B shows a cross-sectional view of the engagement of the threaded rod 506A with the engagement portion 508A (the engagement of the threaded rod 506B and engagement portion 508B can be similar). As shown, the threaded rod 506A can rotate freely within the engagement portion 508A.

In order to insert implant 500, a physician can cut through a patient's skin and soft tissue and create an orifice through the patient's thyroid lamina, as described above. The orifice can have an elongated shape which is substantially longer along the axis A2 (FIG. 2) than along the axis A3 (FIG. 2). The physician can then introduce the implant 500 through the orifice with the longest dimension of its main body 502 aligned with the axis A2. Once the implant 500 has been inserted through the patient's thyroid lamina, the physician can rotate the main body 502 of the implant 500 about axis A1 (FIG. 2) such that the longest dimension of the main body 502 of the implant 500 is generally aligned with and parallel to the axis A3 (FIG. 2). In this configuration, the length of main body 502 of the implant 500 along axis A3 can be greater than the length of the orifice along the axis A3. Thus, by rotating the main body 502 in this way, the implant 500 can be effectively locked in place, prevented from lateral movement through the thyroid lamina.

In some cases, a plurality of implants 500 can be inserted in this manner through such an orifice. For example, a physician can insert a first implant 500 in this manner such that the engagement portions 508A, 508B engage a posterior portion of the patient's paralyzed vocal cord. The physician can then insert a second implant 500 such that the engagement portions 508A, 508B engage an anterior portion of the patient's paralyzed vocal cord. The physician can then insert a third implant 500 such that the engagement portions 508A, 508B of the third implant 500 engage a portion of the patient's vocal cord between the posterior and anterior portions engaged by the first and second implants 500. Using a plurality of implants 500 can increase the customizability of treatment a physician can provide a patient. The physician can select the number of implants for use, the locations of the implants with respect to a paralyzed vocal cord, the shapes and sizes of the engagement portions of each of the implants, etc.

Once one or more implants 500 have been introduced through the orifice and rotated in this way, the physician can adjust the locations of the respective engagement portions 508A, 508B along (or in a direction parallel or substantially parallel to) axis A1. Rather than pushing the pistons 506A, 506B through the main body 502 and sleeve 504, however, a physician can thread the rods 506A, 506B through the main body 502 and sleeve 504 to the desired location(s), and then trim off any excess length of the pistons 506A, 506B. Because the rods 506A, 506B are free to rotate with respect to the engagement portions 508A, 508B, rotation of the rods 506A, 506B does not cause as much trauma to the native tissues as might occur if the rods 506 were not free to rotate with respect to the engagement portions 508. Because the rods are then retained in place against lateral motion with respective to the main body 502 by the engagement of the threaded rods with the main body 502 and sleeve 504, the caps described above with respect to implant 400 can be optional.

Threaded rods such as rods 506A, 506B, corresponding engagement portions such as engagement portions 508A, 508B, and corresponding methods of insertion such as those described with regard to implant 500, can be used in any of the embodiments described herein. For example, threaded rods can be used in place of pistons 406, 606, 706, 806, 906, and/or 1002. Similarly, a non-threaded piston such as piston 406, corresponding retaining element such as cap 414, and corresponding methods of insertion such as those described above with regard to implant 400, can be used in any of the embodiments described herein. For example, non-threaded pistons can be used in place of threaded rods 506.

FIGS. 15-18 illustrate four additional thyroplant implants 600, 700, 800, and 900, respectively. Implant 600 (FIG. 15) includes a main body 602, a sleeve 604, a piston 606, and an engagement portion 608. Implant 700 (FIG. 16) includes a main body 702, a sleeve 704, a piston 706, and an engagement portion 708. Implant 800 (FIG. 17) includes a main body 802, a sleeve 804, a piston 806, and an engagement portion 808. Implant 900 (FIG. 18) includes a main body 902, a sleeve 904, a piston 906, and an engagement portion comprising several cylindrical ribs 908 (e.g., ribs 908A, 908B, 908C) extending away from a medial end portion of the piston 906. The ribs 908 can be interconnected by respective webs 910 (e.g., webs 910A, 910B) which can comprise an elastomeric material.

Each of the implants 600, 700, 800, and 900 can have additional components, such as any of the components described above with regard to implants 400 and 500 (e.g., a cap such as cap 414 and lumen extending through the main body and sleeve). Each of the implants 600, 700, 800, and 900 can function in a manner similar to that described above with regard to implants 400 and 500 (e.g., the respective main bodies and sleeves can have internal lumen through which the respective pistons can travel). The main bodies 602, 702, 802, and 902, sleeves 604, 704, 804, and 904, and pistons 606, 706, 806, and 906 can have similar shapes to one another. In one specific embodiment, each of the respective main bodies can have an overall length L9 of 16 mm, width W9 of 4 mm, and depth D9 of 3 mm, and each of the respective sleeves can have an overall length L10 of 6 mm, width W10 of 4 mm, and depth D10 of 2.5 mm. Each of the main bodies and sleeves can include a lumen having a diameter of about 3 mm extending through it. Each of the pistons can have an overall length L11 of 15 mm and a diameter D11 of about 3 mm (i.e., a diameter that allows it to pass through the lumen in the respective main body and sleeve).

Figure 15:
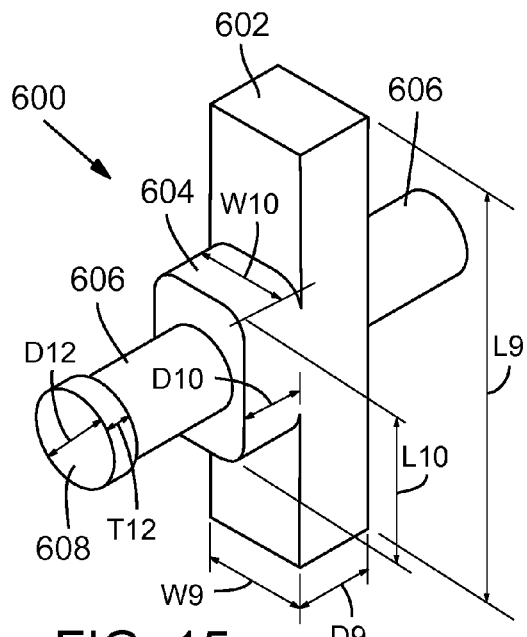
FIG. 15 illustrates another embodiment of a thyroplant implant.
Figure 16:
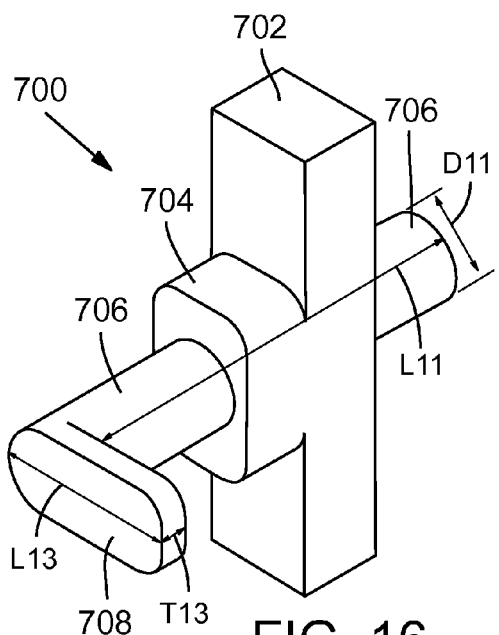
FIG. 16 illustrates another embodiment of a thyroplant implant.

As shown in FIGS. 15-18, engagement portions can have various shapes and sizes. In some cases, a kit can comprise a main body and sleeve together with various pistons, each coupled to engagement portions of different shapes and/or sizes (e.g., a small size such as an engagement portion 608 having a diameter D12 of 3 mm, a medium size such as an engagement portion 608 having a diameter D12 of 3.5 mm, and a large size such as an engagement portion 608 having a diameter D12 of 4 mm). As shown in FIG. 15, an engagement portion 608 can have a generally circular shape with a diameter D12 of about 3 mm, about 3.5 mm, or about 4 mm, and a thickness T12 of about 1 mm. As shown in FIG. 16, an engagement portion 708 can have a generally oblong shape offset from a central longitudinal axis of the piston 706. In some cases, such a shape can be advantageous because it can allow the engagement portion to engage a greater extent of a paralyzed vocal cord. For example, the implant 700 can be inserted such that the oblong engagement portion 708 extends anteriorly along axis A2 along the patient's paralyzed vocal cord, or such that the oblong engagement portion 708 extends posteriorly along axis A2 along the patient's paralyzed vocal cord. In one specific embodiment, the engagement portion 708 can have a thickness T13 of 1 mm and a length L13 of 5 mm.

Figure 17:
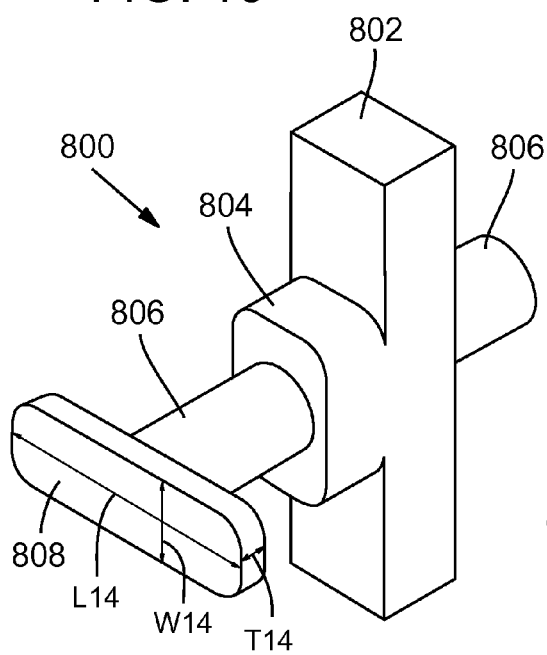
FIG. 17 illustrates another embodiment of a thyroplant implant.

As shown in FIG. 17, an engagement portion 808 can have a generally oblong shape centered on a central longitudinal axis of the piston 806. In some cases, such a shape can be advantageous because it can allow the engagement portion to engage a greater extent of a paralyzed vocal cord. For example, the implant 800 can be inserted such that the oblong engagement portion 808 extends both anteriorly and posteriorly along axis A2 along the patient's paralyzed vocal cord. In one specific embodiment, the engagement portion 808 can have a thickness T14 of 1 mm, a width W14 of 3 mm, and an overall length of 10 mm. In alternative embodiments, engagement portions having various alternative shapes can be used, such as shapes including ovals, squares, triangles, stars, cruciform shapes, etc. In some cases, a kit can include pistons coupled to engagement portions of a variety of different shapes, such as each of the shapes just listed.

An additional advantage of the various shapes of the engagement portions 608, 708, 808 shown in FIGS. 15-17 is that they can allow a physician to select the area of contact between the engagement portion and the paralyzed vocal cord. For example, a physician can select a smaller engagement portion (e.g., engagement portion 608) for an implant to be situated closer to an anterior portion of the vocal cord, as less force is required to medialize this portion of the vocal cord and thus less area is required to adequately spread out the force. Similarly, a physician can select a larger engagement portion (e.g., engagement portion 808) for an implant to be situated closer to a posterior portion of the vocal cord, as greater force is required to medialize this portion of the vocal cord and thus a greater surface area can be used to adequately spread out the force. Use of an oblong engagement portion (e.g., engagement portion 708 or 808) can also be advantageous because they can be used to apply pressure to areas of a paralyzed vocal cord not directly aligned with the orifice created in the thyroid lamina.

Figure 18:
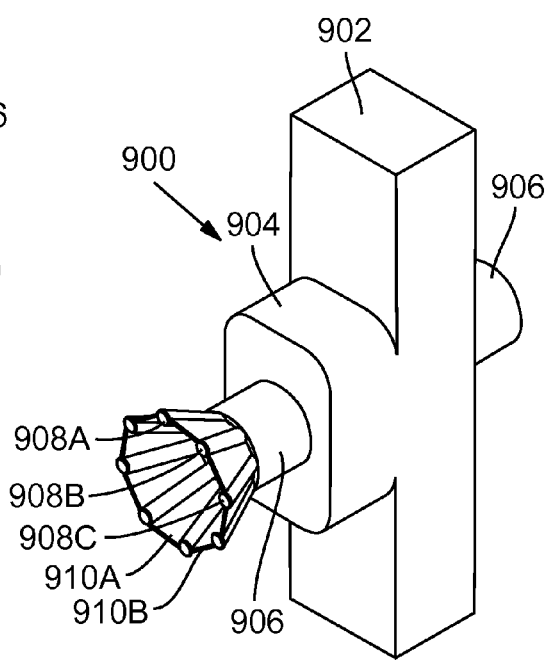
FIG. 18 illustrates another embodiment of a thyroplant implant.

As shown in FIG. 18, an engagement portion can include a plurality of ribs 908 which can pivot radially with respect to a central axis of the piston 906 (e.g., from a radially collapsed position to a radially expanded position) and can be interconnected by a plurality of elastic webs 910. In such an embodiment, as a physician pushes the piston 906 through the main body 902 and sleeve 904, causing the engagement portion to engage a patient's vocal cord and increasing the force being exerted against the vocal cord, the elastic webs 910 can deform and thus the engagement portion can expand in accordance with increased force being exerted against the paralyzed vocal cord. This can be advantageous because it can allow the spreading out of forces over a greater area of native tissue as the force being exerted increases.

In order to insert one of the implants 600, 700, 800, or 900, a physician can cut through a patient's skin and soft tissue and create an orifice through the patient's thyroid lamina, as described above. The orifice can have an elongated shape which is substantially longer along the axis A2 (FIG. 2) than along the axis A3 (FIG. 2). The physician can then introduce the implant through the orifice with the longest dimension of its main body (i.e., dimension L9) aligned with and parallel to the axis A2. Once the implant has been inserted through the patient's thyroid lamina, the physician can rotate the main body of the implant about axis A1 (FIG. 2) such that the longest dimension of the main body of the implant is generally aligned with and parallel to the axis A3 (FIG. 2). In this configuration, the length of main body of the implant along axis A3 can be greater than the length of the orifice along the axis A3. Thus, by rotating the main body in this way, the implant can be effectively locked in place, prevented from lateral movement through the thyroid lamina. Once the implant has been introduced through the orifice and rotated in this way, the physician can adjust the location of the respective engagement portion along axis A1 and lock the piston in place, as described above with regard to implant 400.

In some cases, a plurality of implants can be inserted in this way, as described above with respect to implant 500. For example, three implants 600, or three implants 700, or three implants 800, or three implants 900, or any number and combination of the implants 500, 600, 700, 800, 900 can be inserted as described above with regard to implant 500.

FIGS. 19-20 show another embodiment of an engagement portion 1000 coupled to a piston 1002, which can be used, for example, in combination with the main bodies and sleeves described above. The engagement portion 1000 includes a plurality of ribs 1004 coupled to a plurality of respective paddles 1006 interconnected by a plurality of respective elastomeric bands 1010. In such an embodiment, as a physician pushes the piston 1002 through a main body and sleeve, causing the engagement portion 1000 to engage a patient's vocal cord and increasing the force being exerted against the vocal cord, the elastomeric bands 1010 can deform (and the ribs 1004 can rotate with respect to the piston 1002 at rotation points 1008) and thus the engagement portion 1000 can expand in accordance with increased force being exerted against the paralyzed vocal cord. This can be advantageous because it can allow the spreading out of forces over a greater area of native tissue as the force being exerted increases. FIG. 19 shows the engagement portion 1000 in an open configuration and FIG. 20 shows the engagement portion 1000 in a closed configuration. The elastomeric bands 1010 can be made of natural rubber or any of various suitable synthetic elastomers, such as silicone rubber or polyurethane.

Figure 21:
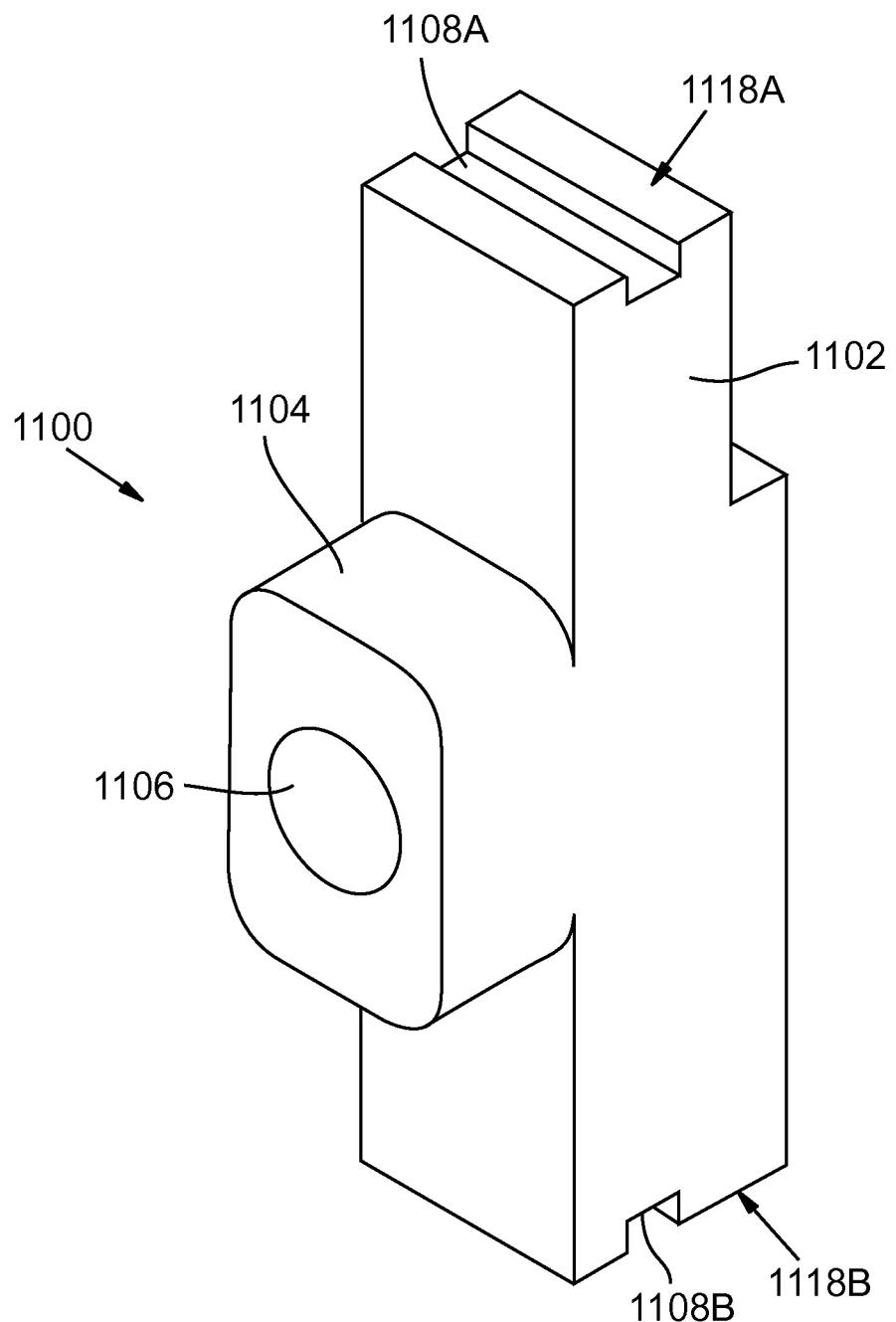
FIGS. 21-23 illustrate portions of a thyroplant implant.
Figure 22:
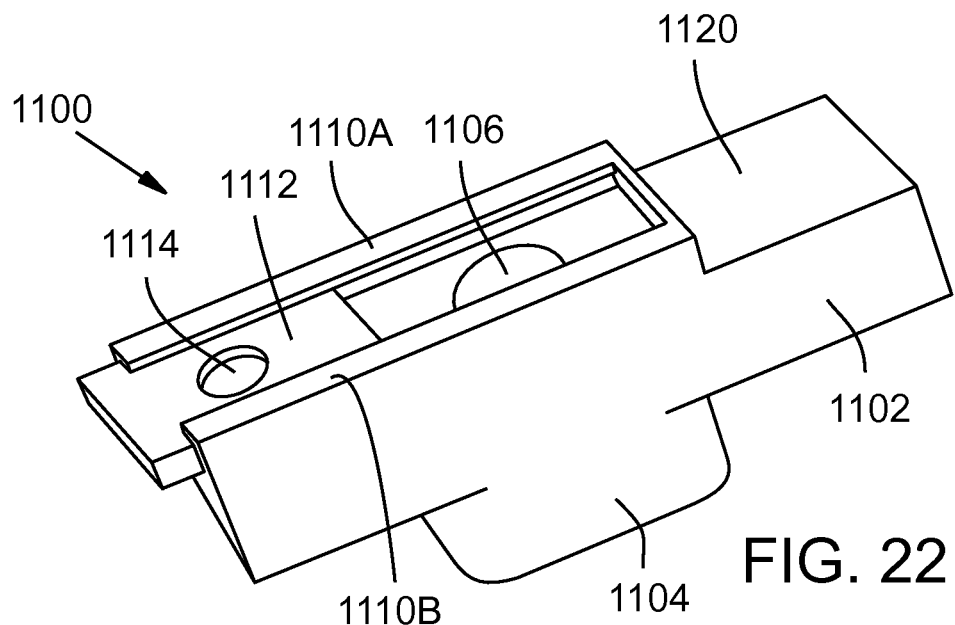
Figure 23:
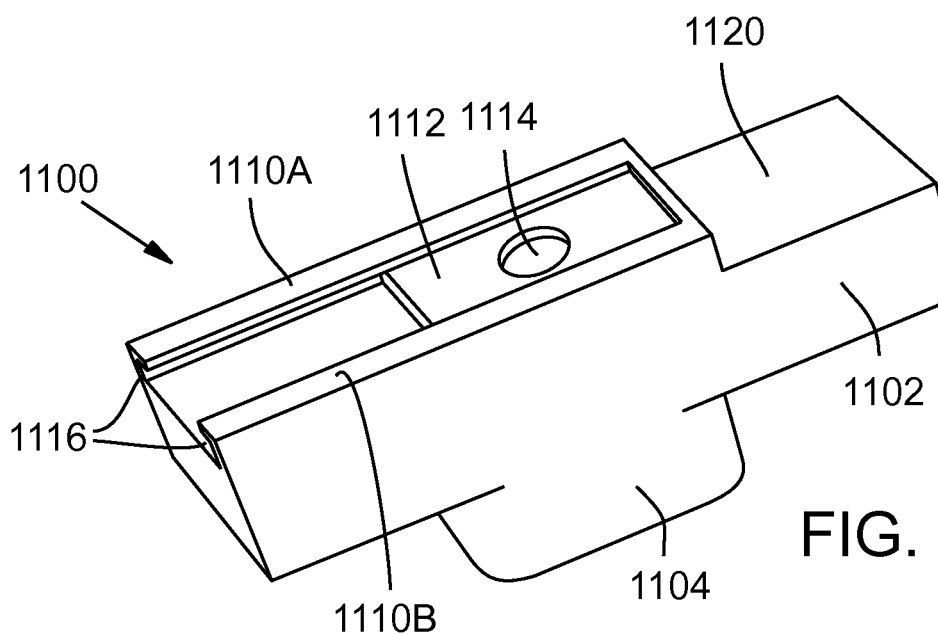

FIGS. 21-23 show an apparatus 1100 which can be used in combination with any of the pistons and/or engagement portions described herein to form a thyroplant implant. Apparatus 1100 includes a main body 1102, a sleeve 1104, and a lumen 1106 extending through the main body 1102 and sleeve 1104. Apparatus 1100 also includes a pair of slots 1108A, 1108B formed in opposing side surfaces 1118A, 1118B of the main body 1102, a pair of retaining elements 1110A, 1110B coupled to or formed in a lateral surface 1120 of the main body 1102, the retaining elements 1110A, 1110B forming a pair of respective slots 1116 through which a piston-retaining element 1112 can slide. An access opening 1114 can be formed in the piston-retaining element 1112 and can allow a physician access to the lumen 1106 and can facilitate adjustment of the location of the piston-retaining element 1112 (e.g., a physician can move the element 1112 by gripping it at the opening 1114). In other embodiments, the apparatus 1100 does not include such an opening 1114.

In order to implant the apparatus 1100, a physician can cut through a patient's skin and soft tissue and create an orifice through the patient's thyroid lamina, as described above. The physician can then introduce the implant such that peripheral edges of the thyroid lamina surrounding the orifice fit within the slots 1108A, 1108B of the apparatus 1100. This can help to retain the apparatus 1100 against movement relative to the patient's paralyzed vocal cord (e.g., migration within the patient's body, or extrusion of the device through the orifice formed in the thyroid lamina.

The apparatus 1100 can be used in combination with any of the various pistons and engagement portions described herein. After the apparatus 1100 has been inserted, a physician can position the piston within the lumen 1106 to medialize the patient's paralyzed vocal cord, remove excess lengths of the piston, and can then slide the piston-retaining element 1112 through the slots 1116 until the piston-retaining element 1112 engages a lateral end portion of the piston to prevent it sliding laterally through the lumen 1106. The apparatus 1100 and piston used therewith can be more easily adjusted than other known implants because, for example, a physician can adjust the piston by simply sliding the piston-retaining element 1112 to expose the piston and then adjusting the location of the piston by sliding it through the lumen 1106 (e.g., by allowing the piston to move laterally through the lumen 1106 and removing an excess length of the piston, or by pushing the piston medially through the lumen 1106 and inserting additional material into the lumen before sliding the piston-retaining element 1112 back through the slots to prevent the piston and additional material sliding laterally through the lumen 1106).

Mechanisms including slots such as slots 1116 and a corresponding retaining element such as retaining element 1112, and corresponding methods, such as those described with regard to apparatus 1100, can be used in any of the embodiments described herein. For example, any of main body portions 402, 502, 602, 702, 802, and/or 902 can include such mechanisms. Similarly, a retaining element such as cap 414 and corresponding methods of insertion, such as those described above with regard to implant 400, can be used in any of the embodiments described herein. For example, a retaining element such as cap 414 can be used in place of the slots 1116 and retaining element 1112 of apparatus 1100, or in place of the slots 1216 and retaining element 1212 of apparatus 1200 (described below). Similarly, any of the embodiments described herein can include slots such as slots 1108A, 1108B, and can be inserted using the corresponding methods described with regard to the apparatus 1100. For example, any of main body portions 402, 502, 602, 702, 802, and/or 902 can include such features.

Figure 24:
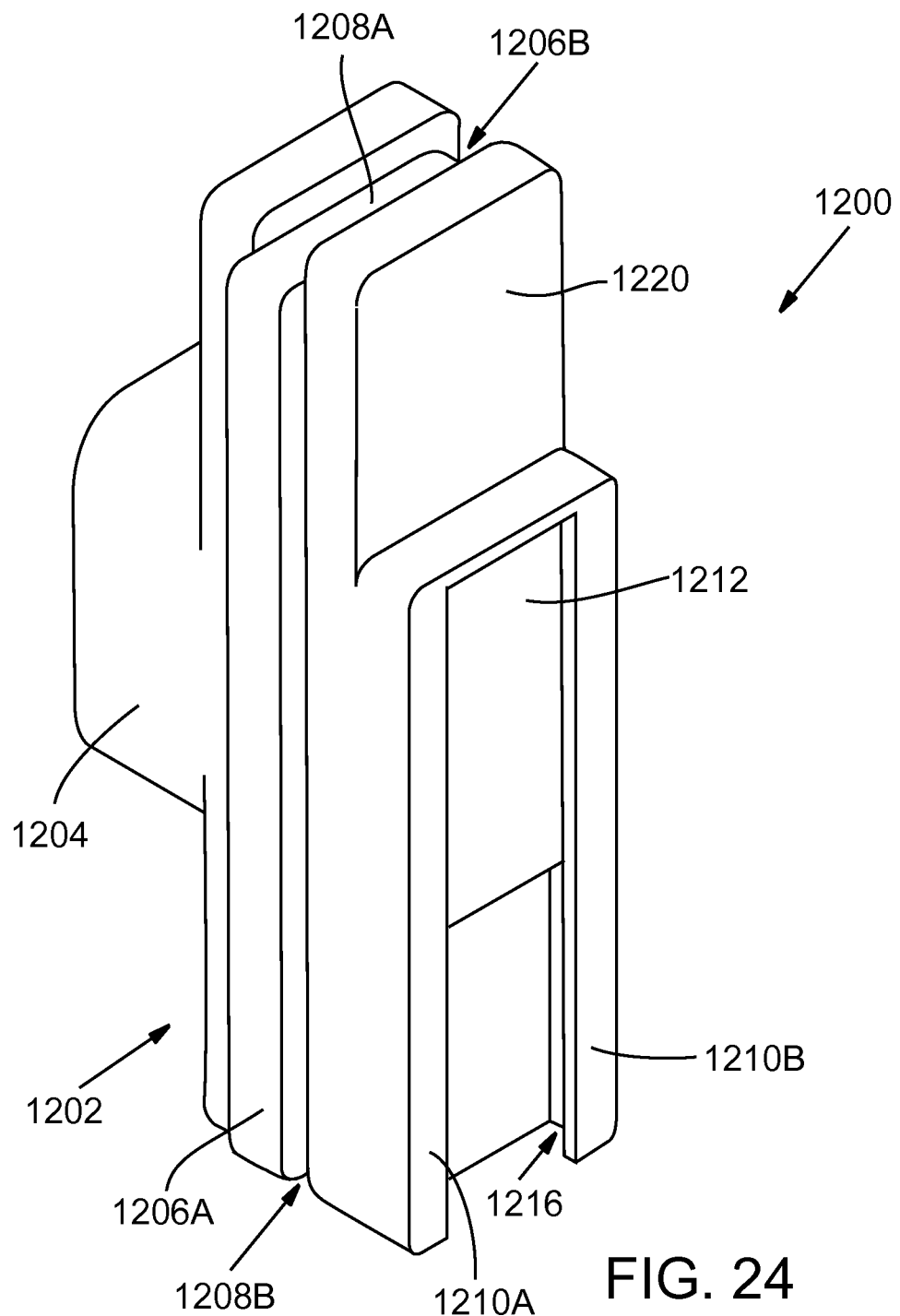
FIG. 24 illustrates a portion of a thyroplant implant.

FIG. 24 shows an apparatus 1200 which can be used in combination with any of the pistons and/or engagement portions described herein to form a thyroplant implant. Apparatus 1200 includes a main body 1202, a sleeve 1204, and a lumen extending through the main body 1202 and sleeve 1204. Apparatus 1200 also includes a pair of slots 1208A, 1208B formed in opposing side surfaces of the main body 1202, a pair of retaining elements 1210A, 1210B coupled to or formed in a lateral surface 1220 of the main body 1202, the retaining elements 1210A, 1210B forming a pair of respective slots 1216 through which a piston-retaining element 1212 can slide. Apparatus 1200 also includes a protruding tongue 1206A and a corresponding groove 1206B formed in opposing side surfaces of the main body 1202. Corners of the apparatus 1200 can be rounded, which can reduce damage caused to native tissue by the apparatus 1200.

In order to implant the apparatus 1200, a physician can cut through a patient's skin and soft tissue and create an orifice through the patient's thyroid lamina, as described above. The physician can then introduce the apparatus 1200 such that peripheral edges of the thyroid lamina surrounding the orifice fit within the slots 1208A, 1208B of the apparatus 1200. This can help to retain the apparatus 1200 against movement relative to the patient's paralyzed vocal cord.

The apparatus 1200 can be used in combination with any of the various pistons and engagement portions described herein. After the apparatus 1200 has been inserted, a physician can position the piston within the lumen of the apparatus 1200 to medialize the patient's paralyzed vocal cord, remove excess lengths of the piston, and can then slide the piston-retaining element 1212 through the slots 1216 until the piston-retaining element 1212 engages a lateral end portion of the piston to prevent it sliding laterally through the lumen of the apparatus 1200. The apparatus 1200 and piston used therewith can be more easily adjusted than other known implants because, for example, a physician can adjust the piston by simply sliding the piston-retaining element 1212 to expose the piston and then adjusting the location of the piston by sliding it through the lumen of the apparatus 1200 (e.g., by allowing the piston to move laterally through the lumen and removing an excess length of the piston, or by pushing the piston medially through the lumen and inserting additional material into the lumen before sliding the piston-retaining element 1212 back through the slots 1216 to prevent the piston and additional material sliding laterally through the lumen).

More than one apparatus 1200 can be implanted into an orifice in a patient's thyroid lamina. For example, after a physician implants a first apparatus 1200, as described above, the physician can implant a second apparatus 1200 following the same procedure described above, such that the tongue 1206A of the first apparatus 1200 fits within the groove 1206B of the second apparatus 1200. If suitable, a physician can implant a third apparatus 1200 following the same procedure, such that the tongue 1206A of the second apparatus 1200 fits within the groove 1206B of the third apparatus. A physician can implant as many apparatuses 1200 as is suitable for the particular patient. In some cases, a physician can implant the apparatuses 1200 such that their respective tongues 1206A and grooves 1206B are generally aligned along axis A3 (FIG. 2). In other cases, a physician can implant the apparatuses 1200 such that their respective tongues 1206A and grooves 1206B are generally aligned along axis A2 (FIG. 2). In some cases, a physician can implant apparatuses 1200 such that they substantially fill the orifice formed in the patient's thyroid lamina.

Any of the devices described herein can include tongues and grooves such as tongue 1206A and groove 1206B of apparatus 1200. For example, any of main body portions 402, 502, 602, 702, 802, 902, and/or 1102 can include such features. Similarly, any of the devices described herein can be inserted using the corresponding methods described with regard to the tongue 1206A and groove 1206B of the apparatus 1200.

Any of the devices described herein can be formed from a variety of biocompatible materials including metals (e.g., titanium), polymers, or plastics. Some of the components can be fabricated from a material sold under the name MEDPOR by the Stryker company. Materials can be selected to promote desirable characteristics of the device, and can be coated with various substances which can increase tissue ingrowth or cell adhesion, decrease migration of the device in a patient's body, or otherwise influence relevant characteristics and the performance of the device. Any of the components described herein can be fabricated using 3D printing techniques, as known in the art.

Any of the devices described herein can be implanted in a patient under local anesthetic, and can be tested during implantation by observing real-time improvements to the patient's phonation. The thyroplant implants described herein provide advantages not available with prior implants, including, in some embodiments, adjustability in three dimensions. Specifically, an implant can be adjusted in the medial-lateral dimension by adjusting the length of a central strut, and in the anterior-posterior and superior-inferior dimensions by adjusting the length of a plurality of arms Implants can be adjusted in each of these dimensions after the initial positioning of the implant in the body, thus, adjustment does not require time consuming and traumatic removal and re-insertion of the implant.

The additional flexibility of the implants described herein allows a single device to be customized by a physician for individual patients rapidly during a single operation. The devices described herein thus decrease the required time of operation, thereby reducing temporary edema and improving results, particularly in long term phonation abilities. These devices also simplify medialization thyroplasty procedures, enabling physicians with a greater range of experience to perform the procedure. In addition, the increased adjustability of the devices described herein, particularly in the posterior and medial directions, can allow a physician to use the devices to close large posterior gaps between the vocal cords, thereby allowing the patient to avoid a later procedure, known as arytenoid adduction, to prevent aspiration.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. As used herein, the terms "a", "an" and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C" or "A, B and C."

As used herein, the term "coupled" generally means physically coupled or linked and does not exclude the presence of intermediate elements between the coupled items absent specific contrary language.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A prosthetic apparatus for displacing a vocal cord comprising:
   a main body portion configured to be implanted against a thyroid lamina of a patient, the main body portion having a medial surface and a lateral surface and a plurality of lumen extending through the main body from the medial surface to the lateral surface of the main body;
   a plurality of engagement elements configured to engage a paralyzed vocal cord of a patient; and
   a plurality of pistons, each of the pistons having a first end portion situated within a respective one of the lumen of the main body and a second end portion coupled to a respective one of the engagement elements.

2. The apparatus of claim 1, wherein each of the pistons is axially adjustable within the respective lumen of the main body.

3. The apparatus of claim 1, further comprising a plurality of hollow sleeves, each of the sleeves having a respective lumen extending therethrough, wherein each of the lumen of the sleeves is in communication with a respective lumen of the main body, and wherein each of the pistons extends through a respective one of the lumen of the sleeves.

4. The apparatus of claim 3, wherein the sleeves are coupled to the medial surface of the main body.

5. The apparatus of claim 1, wherein the plurality of lumen of the main body are spaced apart from each other along a single axis from a first end of the main body to a second end of the main body.

6. The apparatus of claim 5, wherein:
   the plurality of lumen of the main body includes a first lumen situated closest to the first end of the main body, a second lumen situated closest to the second end of the main body, and a third lumen situated between the first lumen and the second lumen along the single axis;
   the plurality of pistons comprises a first piston having a first end portion situated within the first lumen and a second end portion coupled to a first engagement element, a second piston having a first end portion situated within the second lumen and a second end portion coupled to a second engagement element, and a third piston having a first end portion situated within the third lumen and a second end portion coupled to a third engagement element; and
   the third engagement element is larger than the first engagement element and the second engagement element is larger than the third engagement element.

7. The apparatus of claim 6, wherein the first, second, and third engagement elements have a generally circular cross-sectional shape.

* * * * *